United States Patent
Tang et al.

(10) Patent No.: US 11,644,465 B2
(45) Date of Patent: May 9, 2023

(54) ASSAYS, SENSING PLATFORMS, AND METHODS FOR DIAGNOSIS OF CORONAVIRUS INFECTION AND RE-INFECTION

(71) Applicant: Nirmidas Biotech, Inc., Palo Alto, CA (US)

(72) Inventors: Meijie Tang, Cupertino, CA (US); Hongjie Dai, Cupertino, CA (US); Tiancheng Liu, Union City, CA (US); Jessica Hsiung, Livermore, CA (US); Jessica Kost, Santa Clara, CA (US); Deepika Sreedhar, San Jose, CA (US); Su Zhao, Santa Clara, CA (US)

(73) Assignee: Nirmidas Biotech, Inc., Palo Alto, CA (US)

( * ) Notice: Subject to any disclaimer, the term of this patent is extended or adjusted under 35 U.S.C. 154(b) by 0 days.

(21) Appl. No.: 17/348,665

(22) Filed: Jun. 15, 2021

(65) Prior Publication Data
US 2021/0389322 A1 Dec. 16, 2021

Related U.S. Application Data

(60) Provisional application No. 63/039,046, filed on Jun. 15, 2020.

(51) Int. Cl.
*G01N 33/569* (2006.01)
*G01N 33/553* (2006.01)
*G01N 21/64* (2006.01)

(52) U.S. Cl.
CPC ... *G01N 33/56983* (2013.01); *G01N 21/6428* (2013.01); *G01N 33/553* (2013.01); *G01N 2021/6439* (2013.01); *G01N 2469/20* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| 9,823,246 B2 | 11/2017 | Dai et al. |
| 11,088,478 B2 | 8/2021 | Ho et al. |
| 2016/0025744 A1 | 1/2016 | Feldman et al. |
| 2020/0158728 A1 | 5/2020 | Robinson et al. |

FOREIGN PATENT DOCUMENTS

CN 105693906 A 6/2016

OTHER PUBLICATIONS

Zhang, B. et al. An Integrated Peptide-Antigen Microarray on Plasmonic Gold Films for Sensitive Human Antibody Profiling, PLOS One, Jul. 2013 vol. 8, Issue 7, e71043 (Year: 2013).*

(Continued)

*Primary Examiner* — Xiaoyun R Xu
(74) *Attorney, Agent, or Firm* — Squire Patton Boggs (US)

(57) ABSTRACT

Disclosed herein are methods for diagnosing or prognosticating SARS-CoV-2 infection and/or COVID-19 in a subject. The methods set forth improved immunoassays, sensing platforms, and methods for detecting SARS-CoV-2 infection and re-infection.

29 Claims, 7 Drawing Sheets
(7 of 7 Drawing Sheet(s) Filed in Color)

(56) References Cited

OTHER PUBLICATIONS

Taghavian, O. et al. Antibody Profiling by Proteome Microarray with Multiplex Isotype Detection Reveals Overlap between Human and Aotus nancymaae Controlled Malaria Infections, Proteomics. 2018, 18, 1700277 (Year: 2018).*

Huang, C. et al. Rapid Detection of IgM Antibodies against the SARS-CoV-2 Virus via Colloidal Gold Nanoparticle-Based Lateral-Flow Assay, ACS Omega 2020, 5, 12550-12556 (Year: 2020).*

He, Y. et al. Receptor-binding domain of SARS-CoV spike protein induces highly potent neutralizing antibodies: implication for developing subunit vaccine, Biochemical and Biophysical Research Communications 324 (2004) 773-781 (Year: 2004).*

Trivedi, S. et al. Development and Evaluation of a Multiplexed Immunoassay for Simultaneous Detection of Serum IgG Antibodies to Six Human, Scientific Reports | (2019) 9:1390 (Year: 2019).*

Souza, V., et al. Use of an Immunoglobulin G Avidity Test To Discriminate between Primary and Secondary Dengue Virus Infections, Journal of Clinical Microbiology, Apr. 2004, p. 1782-1784 (Year: 2004).*

Kim, S. et al. A Novel Synonymous Mutation of SARS-CoV-2: Is This Possible to Affect Their Antigenicity and Immunogenicity?, Vaccines, 2020, 8, 220 (Year: 2020).*

To, K. et al. Temporal profiles of viral load in posterior oropharyngeal saliva samples and serum antibody responses during infection by SARS-CoV-2: an observational cohort study, Lancet Infection Disease, 20: 565-574 (Year: 2020).*

Adams, E.R., et al. Antibody testing for COVID-19: A report from the National COVID Scientific Advisory Panel. medRxiv, 2020. 2004.2015.20066407 (2020).

Amanat, F., et al. A serological assay to detect SARS-CoV-2 seroconversion in humans. Nat Med (2020).

Batéjat, C., Grassin, Q., Manuguerra, J.-C. & Leclercq, I. Heat inactivation of the Severe Acute Respiratory Syndrome Coronavirus 2. bioRxiv, 2020.2005.2001.067769 (2020).

Bendavid, E., et al. COVID-19 Antibody Seroprevalence in Santa Clara County, California. medRxiv, 2020.2004.2014.20062463 (2020).

Burbelo, P.D., et al. Sensitivity in Detection of Antibodies to Nucleocapsid and Spike Proteins of Severe Acute Respiratory Syndrome Coronavirus 2 in Patients With Coronavirus Disease 2019. The Journal of Infectious Diseases; 2020; XX:pp. 1-8; DOI: 10.1093/infdis/jiaa273 (2020).

Chen, X., et al. A novel quantitative microarray antibody capture assay identifies an extremely high hepatitis delta virus prevalence among hepatitis B virus-infected mongolians. Hepatology 66, 1739-1749; oi:10.1002/hep.28957 (2017).

Chen et al., "Direct water-phase synthesis of lead sulfide quantum dots encapsulated by β-lactoglobulin for in vivo second near infrared window imaging with reduced toxicity", Chem. Commun. 2016 52: 4025-4028; DOI: 10.1039/c6cc00099a.

Corman, V.M., et al. Detection of 2019 novel coronavirus (2019-nCoV) by real-time RT-PCR. Euro surveillance : bulletin Europeen sur les maladies transmissibles = European communicable disease bulletin 25(2020).

De Souza, V.A.U.F., et al. Use of an Immunoglobulin G Avidity Test To Discriminate between Primary and Secondary Dengue Virus Infections. Journal of clinical microbiology vol. 42, No. 4, 1782-1784; DOI: 10.1128/JCM.42.4.1782-1784.2004 (2004).

Furuya, A.K.M., et al. Use of the immunoglobulin G avidity assay to differentiate between recent Zika and past dengue virus infections. Clin Sci (Lond) 133, 859-867; https://doi.org/10.1042/CS20180874 (2019).

Granger, D., et al. Serologic Testing for Zika Virus: Comparison of Three Zika Virus IgM-Screening Enzyme-Linked Immunosorbent Assays and Initial Laboratory Experiences. Journal of clinical microbiology, vol. 55, Issue 7, pp. 2127-2136; https://doi.org/10.1128/JCM.00580-17 (2017).

Gutierrez, J. & Maroto, C. Are IgG antibody avidity assays useful in the diagnosis of infectious diseases? A review. Microbios 87, 113-121 (1996).

He et al., "Receptor-Binding Domain of SARS-CoV Spike Protein Induces Highly Potent Neutralizing Antibodies: Implication for Developing Subunit Vaccine", Biochemical and Biophysical Research Communications 324 (2004) 773-781.

Hedman, K. & Seppala, I. Recent rubella virus infection indicated by a low avidity of specific IgG. J Clin Immunol 8, 214-221 (1988).

Hou et al., "Detection of IgM and IgG Antibodies in Patients with Coronavirus Disease 2019", Clinical & Translational Immunology 2020; e1136.doi: 10.1002/cti2.1136.

Huang et al., "Rapid Detection of IgM Antibodies Against the SARS-CoV-2 Virus Via Colloidal Gold Nanoparticle-Based Lateral-Flow Assay", ACS Omega 2020, 5, 12250-12256.

Huang et al., "Development of NIR-II Fluorescence Image-Guided and PH-Responsive Nanocapsules for Cocktail Drug Delivery", Nano Research 2015 8(6):1932-1943; DOI 10.1007/s12274-015-0702-5.

Infantino, M., et al. Diagnostic accuracy of an automated chemiluminescent immunoassay for anti-SARS-CoV-2 IgM and IgG antibodies: an Italian experience. Journal of medical virology (2020).

Kashir, J. & Yaqinuddin, A. Loop mediated isothermal amplification (LAMP) assays as a rapid diagnostic for COVID-19. Med Hypotheses 141, 109786; https://doi.org/10.1016/J.Mehy.2020.109786 (2020).

Kim et al., "A Novel Synonymous Mutation of SARS-CoV-2: Is This Possible to Affect Yheir Antigenicity and Immunogenicity", Vaccines 2020, 8, 220; doi:10.3390/Vaccines8020220.

Lassaunière, R., et al. Evaluation of nine commercial SARS-CoV-2 immunoassays. medRxiv, 2020.2004.2009.20056325 (2020).

Levesque, J. & Maybury, D.W. A note on COVID-19 seroprevalence studies: a meta-analysis using hierarchical modelling. medRxiv, pp. 1-20, doi.org/10.1101/2020.05.03.20089201 (2020).

Li, X., et al. Multiplexed Anti-Toxoplasma IgG, IgM, and IgA Assay on Plasmonic Gold Chips: towards Making Mass Screening Possible with Dye Test Precision. Journal of clinical microbiology vol. 54, No. 7, 1726-1733; doi:10.1128/JCM.03371-15. (2016).

Li, X., et al. Plasmonic gold chips for the diagnosis of Toxoplasma gondii, CMV, and rubella infections using saliva with serum detection precision. European journal of clinical microbiology & infectious diseases : official publication of the European Society of Clinical Microbiology 38, 883-890; https://doi.org/10.1007/s10096-019-03487-1 (2019).

Lippi, G., et al. Assessment of immune response to SARS-CoV-2 with fully automated MAGLUMI 2019-nCoV IgG and IgM chemiluminescence immunoassays. Clinical chemistry and laboratory medicine 58(7): 1156-1159 (2020).

Liu, W., et al. Evaluation of Nucleocapsid and Spike Protein-Based Enzyme-Linked Immunosorbent Assays for Detecting Antibodies against SARS-CoV-2. Journal of clinical microbiology, vol. 58 Issue 6 e00461-20; pp. 1-7; https://doi.org/10.1128/JCM.00461-20. (2020).

Long, Q.-X., et al. Antibody responses to SARS-CoV-2 in patients with COVID-19. Nature Medicine (2020).

Montesinos, I., et al. Evaluation of two automated and three rapid lateral flow immunoassays for the detection of anti-SARS-CoV-2 antibodies. Journal of clinical virology : the official publication of the Pan American Society for Clinical Virology 128, 104413; doi.org/10.1016/j.jcv.2020.104413 (2020).

Petherick, A. Developing antibody tests for SARS-CoV-2. Lancet 395, 1101-1102 (2020).

Pinto, D., et al. Cross-neutralization of SARS-CoV-2 by a human monoclonal SARS-CoV antibody. Nature, vol. 583, pp. 291-310; https://doi.org/10.1038/s41586-020-2349-y (2020).

Prince, H.E., Yeh, C. & Lapé-Nixon, M. Utility of IgM/IgG Ratio and IgG Avidity for Distinguishing Primary and Secondary Dengue Virus Infections Using Sera Collected More than 30 Days after Disease Onset. Clinical and Vaccine Immunology vol. 18, No. 11, 1951-1956; doi:10.1128/CVI.05278-11 (2011).

Qian et al., "Multicolor polystyrene nanospheres tagged with up-conversion fluorescent nanocrystals", Nanotechnology 19 (2008) 255601 (4pp); Doi: 10.1088/0957-4484/19/25/255601.

(56) References Cited

OTHER PUBLICATIONS

Reifer, J., Hayum, N., Heszkel, B., Klagsbald, I. & Streva, V.A. SARS-CoV-2 IgG Antibody Responses in New York City. medRxiv; 2020; https://doi.org/10.1101/2020.05.23.20111427.

Revello, M.G., et al. Diagnosis and Outcome of Preconceptional and Periconceptional Primary Human Cytomegalovirus Infections. The Journal of Infectious Diseases 186, 553-557 (2002).

Sheridan, C. Convalescent serum lines up as first-choice treatment for coronavirus. Nat Biotechnol 38, 655-658 (2020).

Sood, N., et al. Seroprevalence of SARS-CoV-2-Specific Antibodies Among Adults in Los Angeles County, California, JAMA, vol. 323, No. 23 pp. 2425-2427; April 10-11, 2020.

Suligoi, B., et al. Precision and Accuracy of a Procedure for Detecting Recent Human Immunodeficiency Virus Infections by Calculating the Antibody Avidity Index by an Automated Immunoassay-Based Method. Journal of clinical microbiology, vol. 40, No. 11, 4015-4020; DOI: 10.1128/JCM.40.11.4015-4020.2002 (2002).

Tabakman, S.M., et al. Plasmonic substrates for multiplexed protein microarrays with femtomolar sensitivity and broad dynamic range. Nature Communications 2, 466; pp. 1-9; DOI: 10.1038/ncomms1477 (2011).

Taghavian et al., "Antibody Profiling by Proteome Microarray with Multiplex Isotype Detection Reveals Overlap Between Human and *Aotus nancymaae* Controlled Malaria Infections", Proteomics 2018, 18, 1700277; DOI:10.1002/pmic.201700277.

Tahamtan, A. & Ardebili, A. Real-time RT-PCR in COVID-19 detection: issues affecting the results. Expert Rev Mol Diagn 20, 453-454 (2020); DOI: 10.1080/14737159.2020.1757437.

Tang, M.S., et al. Clinical Performance of the Roche SARS-CoV-2 Serologic Assay. Clinical Chemistry, pp. 1-23 (2020).

Tang, M.S., et al. Clinical Performance of Two SARS-CoV-2 Serologic Assays. Clin Chem 66:8 1107-1109 (2020).

Tao et al., "Biological Imaging Using Nanoparticles of Small Organic Molecules with Fluorescence Emission at Wavelengths Longer than 1000 nm**", Agnew. Chem. Int. Ed. 2013, 52:13002-13006, DOI: 10.1002/anie.201307346.

Theel, E.S., Harring, J., Hilgart, H. & Granger, D. Performance Characteristics of Four High-Throughput Immunoassays for Detection of IgG Antibodies against SARS-CoV-2. Journal of clinical microbiology, JCM.01243-01220 (2020).

To, K.K., et al. Temporal profiles of viral load in posterior oropharyngeal saliva samples and serum antibody responses during infection by SARS-CoV-2: an observational cohort study. Lancet Infect Dis 20, 565-574; https://doi.org/10.1016/S1473-3099(20)30196-1 (2020).

Tre-Hardy, M., et al. Validation of a chemiluminescent assay for specific SARS-CoV-2 antibody. Clinical chemistry and laboratory medicine, 58(8): pp. 1357-1364; https://doi.org/10.1515/cclm-2020-0594 (2020).

Trivedi et al., "Development and Evalusation of a Multiplexed Immunoassay fro Simultaneous Detection of Serum IgG Antibodies to Six Human Coronaviruses", Scientific reports 2019 9:1390; doi.org/10.1038/s41598-018-37747-5.

Vashist, S.K. In Vitro Diagnostic Assays for COVID-19: Recent Advances and Emerging Trends. Diagnostics (Basel) 10, 202; doi:10.3390/daignostics10040202 (2020).

Victora, G.D. & Nussenzweig, M.C. Germinal centers. Annu Rev Immunol 30, 429-457; doi:10.1146/annurev-immunol-020711-075032 (2012).

Walls, A.C., et al. Structure, Function, and Antigenicity of the SARS-CoV-2 Spike Glycoprotein. Cell 181, 281-292 e286; https://doi.org/10.1016/j.cell.2020.02.058 (2020).

Wang, T., Lien, C., Liu, S. & Selveraj, P. Effective Heat Inactivation of SARS-CoV-2. medRxiv,4 pages (2020) 2020.2004.2029.20085498 (2020).

Wu, Y., et al. Identification of Human Single-Domain Antibodies against SARS-CoV-2. Cell Host Microbe 27:891-898; https://doi.org/10.1016/j.chom.2020.04.023 (2020).

Xu, X., et al. Seroprevalence of immunoglobulin M and G antibodies against SARS-CoV-2 in China. Nature Medicine vol. 26: 1193-1195 (2020); https://doi.org/10.1038/s41591-020-0949-6.

Yan, R., et al. Structural basis for the recognition of SARS-CoV-2 by full-length human ACE2. Science 367, 1444-1448 (2020).

Yang et al. "Rational Design of Molecular Fluorophores for Biological Imaging in the NIR-II Window", Adv. Matter. 2017, 291605497 pp. 1-9; DOI: 10.1002/adma.201605497.

Younes, N., et al. Challenges in Laboratory Diagnosis of the Novel Coronavirus SARS-CoV-2. Viruses 12, 582; doi:10.3990/v12060582 (2020).

Yu, L., et al. Rapid Detection of COVID-19 Coronavirus Using a Reverse Transcriptional Loop-Mediated Isothermal Amplification (RT-LAMP) Diagnostic Platform. Clinical Chemistry 66:7 975-986; DOI: 10.1093/clinchem/hvaa102 (2020).

Yuan, M., et al. A highly conserved cryptic epitope in the receptor binding domains of SARS-CoV-2 and SARS-CoV. Science 368, 630-633; 10.1126/science.abb7269 (2020).

Zhang et al., "An Integrated Peptide-Antigen Microarray on Plasmonic Gold Films for Sensitive Human Antibody Profiling", PLOS ONE, Jul. 2013 vol. 8, No. 7 e71043, pp. 1-11.

Zhang, B., et al. Diagnosis of Zika virus infection on a nanotechnology platform. Nat Med vol. 23, No. 5, 548-550; doi:10.1038/nm.4302 (2017).

Zhang, B., Kumar, R.B., Dai, H. & Feldman, B.J. A plasmonic chip for biomarker discovery and diagnosis of type 1 diabetes. Nat Med 20, 948-953; doi:10.1038/nm.3619. (2014).

Zhao, J., et al. Antibody responses to SARS-CoV-2 in patients of novel coronavirus disease 2019. Clinical infectious diseases: an official publication of the Infectious Diseases Society of America (2020).

Li, et al., Plasmonic gold chips for the diagnosis of *Toxoplasma gondii*, CMV, and rubella infections using saliva with serum detection precision, European Journal of Clinical Microbiology & Infectious Diseases (2019) 38:883-890.

Liu, et al., Quantification of antibody avidities and accurate detection of SARS-CoV-2 antibodies in serum and saliva on plasmonic substrates, Nature Biomedical Engineering, vol. 4, Dec. 2020; 1188-1196.

Kaufman, et al., The Diagnostic Applications of Saliva—A Review; Critical Reviews in Oral Biology and Medicine, 13(2): 197-212 (2002).

Loeb, et al., Evaluation of Salivary Antibodies to Detect Infection with *Helicobacter pylori*, Can J. Gastroenterol vol. 11, No. 5 Jul./Aug. 1997.

Patinen, et al., Salivary and Serum IgA Antigliadin Antibodies in Dermatitis Herpetiformis, European Journal of Oral Sciences 1995; 103: 280-284.

\* cited by examiner

ASSAYS, SENSING PLATFORMS, AND METHODS FOR DIAGNOSIS OF CORONAVIRUS INFECTION AND RE-INFECTION

This application claims priority to, and the benefit of, U.S. Provisional Patent Application No. 63/039,046, filed Jun. 15, 2020, the entire contents of which are herein incorporated by reference in its entirety for all purposes.

FIELD OF INVENTION

The present disclosure relates generally to the field of immunoassays and, more specifically, to improved assays, sensing platforms, and methods for diagnosis of SARS-CoV-2, assess recent infection vs. remote infection and analyze antibodies elicited by immune responses to vaccine.

BACKGROUND OF THE INVENTION

The severe acute respiratory syndrome coronavirus 2 (SARS-CoV-2) causes the disease known as COVID-19. Within months, SARS-CoV-2 has rapidly spread throughout the globe, causing millions of infections and deaths. Thus, the outbreak and rapid spread of SARS-CoV-2 virus has led to a dire global pandemic. Globally, almost 150 million people have been infected and more than 3 million have died of COVID-19. In the United States, more than 32 million people have been infected and almost 600,000 have died, and the pandemic continues to spread.

Diagnosis of COVID-19 typically relies on molecular detection of the SARS-CoV-2 virus by RT-PCR or isothermal nucleic acid amplification methods in a narrow time window post infection (see e.g., Corman, V. M., et al. (2020) European communicable disease bulletin 25; Tahamtan, A. & Ardebili (2020) Expert Rev Mol Diagn 20, 453-454; Kashir, J. & Yaqinuddin, A. (2020) Med Hypotheses 141, 109786; Yu, L., et al. (2020) Clinical Chemistry 66(7): 975-977).

Antibody testing is highly complementary to molecular diagnosis and is becoming increasingly important to both the short- and long-term assessment of SARS-CoV-2 infected individuals. A variety of antibody tests have been developed using lateral flow rapid tests, enzyme-linked immunosorbent assay (ELISA) and chemiluminescence platforms, including ones authorized by the U.S. Food and Drug Administration (FDA) for emergency use. However, despite the progress, antibody tests are still lacking in accuracy and specificity and are thus, unable to provide much crucial information that could help stop the pandemic. For example, currently, there are no tests that can assess antibody maturation that could aid in evaluating the timing of infection, and differentiate primary infection from secondary infection. Furthermore, none of the current SARS-CoV-2 antibody tests offer testing of non-invasive matrices such as saliva.

Highly accurate detection of antibodies for SARS-CoV-2 is an indispensable part of the effort to combat the pandemic. A positive antibody test is presumed to mean a person has been infected with SARS-CoV-2 at some point in the past. However, currently available antibody tests are not able to determine the timing of an infection (recent or remote) or if a subject is currently infected, and are thus typically used to ascertain previous infection (see e.g., The Interim Guidelines for COVID-19 Antibody Testing, Centers for Disease Control and prevention, updated Mar. 17, 2021).

High specificity is critical to avoid misinterpretations or false positives, unnecessary stress and quarantine, and to prevent controversies and wrong conclusions for surveillance or prevalence studies. Thus, highly specific and accurate detection of antibodies against SARS-CoV-2 is crucial to combating the pandemic by aiding diagnosis and assessing infection timing, prevalence, duration of antibody response, and potential immunity.

Thus, what is needed in the art are highly specific and accurate methods for detection of antibodies against SARS-CoV-2. Fortunately, the following disclosure provides for this and other needs.

SUMMARY OF THE INVENTION

In one embodiment, disclosed herein is a high accuracy, semi-quantitative assay using the nanostructured plasmonic gold (pGOLD™) platform for detecting IgG, IgM, and IgG avidity against SARS-CoV-2 spike proteins S1 subunit and RBD in human serum and saliva. The pGOLD™ substrate comprises nanoscale gold islands with abundant nanogaps, affording near-infrared (NIR) fluorescence enhancement by up to ~100-fold owing to plasmonic resonance and local electric field enhancements. The greatly increased NIR signal-to-background ratio on pGOLD™ permits multiplexed detection of panels of biological analytes over wide dynamic ranges.

Therefore in one aspect, the disclosure provides a method for diagnosing or prognosticating SARS-CoV-2 infection and/or COVID-19 in a subject, the method comprising: (a) obtaining, or having obtained, a biological sample from the subject; (b) contacting the biological sample to one or more SARS-CoV-2 antigens, wherein the one or more SARS-CoV-2 antigens are bound on a plasmonic substrate, and wherein the one or more SARS-CoV-2 antigens specifically bind to one or more IgM, IgG, or IgA antibody in the biological sample to form immune complexes; (c) contacting the IgG, IgM, or IgA immune complexes with dye labeled antihuman IgG, antihuman IgM and antihuman IgA antibodies, wherein the dye labeled antihuman IgG, antihuman IgM, and antihuman IgA antibodies are each labeled with a different dye that fluoresces at a non-overlapping emission wavelength, and (d) detecting fluorescence intensities of the dyes to diagnose SARS-CoV-2 infection and/or COVID-19, wherein the fluorescence intensity is proportional to the amount of IgM, IgG, or IgA antibody in the sample, and wherein the amount of IgM, IgG, or IgA antibody in the sample indicates the time since SARS-CoV-2 infection, and (e) treating the subject diagnosed with SARS-CoV-2 infection and/or COVID-19 with a compound or other therapy to mitigate symptoms, prevent spread of SARS-CoV-2 infection, facilitate therapy for others, and/or improve symptoms of COVID-19.

In one embodiment, the one or more SARS-CoV-2 antigen is at least two SARS-CoV-2 antigens.

In some embodiments, the plasmonic substrate is a plasmonic gold, silver, aluminum, copper, glass, quartz, plastic or nitrocellulose substrate. In another embodiment, the substrate comprises a metallic film arranged discontinuously on the substrate wherein the metallic film has isolated island areas of between about 100 nm2 and 250,000 nm2 in surface-exposed area, the isolated islands being separated by gaps of about 10 to about 60 nm. In another embodiment, the plasmonic substrate is a plasmonic gold substrate.

In some embodiments, including any of the foregoing, the biological sample is selected from the group consisting of human serum, plasma, whole blood, dried blood spot dissolved in buffer solution, and saliva. In one embodiment, the biological sample is a saliva sample.

In some embodiments, including any of the foregoing, the one or more SARS-CoV-2 antigen is coated on the substrate at distinct locations. In another embodiment, the one or more SARS-CoV-2 antigen is selected from the group consisting of a SARS-CoV-2 S1 subunit, a receptor binding domain (RBD), an S2 subunit and a nucleocapsid protein. In one embodiment, the one or more SARS-CoV-2 antigens are SARS-CoV-2 S1 and RBD. In another embodiment, the one or more SARS-CoV-2 antigen is a SARS-CoV-2 antigen variant selected from the group consisting of variants: (i) N501Y; (ii) K417N, E484K, and N501Y; (iii) E484K; K417N; (iv) L452R and E484Q; (v) K417T, E484K, and N501Y; (vi) K417T; (vii) HV69-70 deletion, a Y144 deletion, N501Y, A570D, D614G, P681H, T716I, S982A, and D1118H; (viii) L18F, D80A, D215G, a LAL242-244 deletion, R246I, K417N, E484K, N501Y, D614G, and A701V; (ix) D80A, K417N, E484K, N501Y, D614G, and A701V; (x) L18F, T20N, P26S, D138Y, R190S, K417T, E484K, N501Y, D614G, H655Y, T1027I, and V1176F; and (xi) L18F, T20N, P26S, D138Y, R190S, K417T, E484K, N501Y, D614G, H655Y, T1027I. In another embodiment, the plasmonic substrate further comprises at least one antigen selected from a MERS antigen, and a common cold antigen selected from the group of human coronaviruses consisting of 229E, NL63, OC43, and HKU1.

In some embodiments, including any of the foregoing, the dyes are Cy3, Cy5, CF647, IRdye800, IR820, or iFluo820.

In some embodiments, including any of the foregoing, the method further comprises adding a protein denaturing agent to the biological sample in step (a). In one embodiment, the protein denaturing agent is selected from urea, formamide, guanidine, sodium salicylate, dimethyl sulfoxide, propylene glycol, and combinations thereof. In one embodiment, the protein denaturing agent is urea or formamide.

In some embodiments, including any of the foregoing, the method further comprises after step (b), adding a protein denaturing agent to destabilize the immune complexes, followed by a rinse step to remove the protein denaturing agent, and thereby removing unbound and low avidity antibodies. In some embodiments, the removing the protein denaturing agent comprises rinsing. In some embodiments, the protein denaturing agent is selected from urea, formamide, guanidine, sodium salicylate, dimethyl sulfoxide, propylene glycol, and combinations thereof. In one embodiment, the protein denaturing agent is urea or formamide.

In some embodiments, including any of the foregoing, the biological sample is collected in a local or remote lab, office, or home and mailed to a clinical lab for testing antibodies against SARS-CoV-2 and other coronaviruses.

In another aspect the disclosure provides a method of diagnosing or prognosticating recent or remote SARS-CoV-2 infection in a subject, wherein the subject was recently infected, remotely infected, or recently and remotely infected; the method comprising: (a) obtaining, or having obtained, a biological sample from the subject; (b) contacting the biological sample to one or more SARS-CoV-2 antigens, wherein the one or more SARS-CoV-2 antigens are bound on a plasmonic substrate, and wherein the one or more SARS-CoV-2 antigen specifically bind to one or more IgM, IgG, IgA antibody in the biological sample to form immune complexes, and wherein the plasmonic substrate is present in a multiple well format such that duplicate substrates are located side-by-side, (c) adding a protein denaturing agent to one of the duplicate substrates either prior to or after step (b), to destabilize the immune complexes, followed by a rinse step to remove the protein denaturing agent, thereby removing unbound and low avidity antibodies, (d) contacting the IgG, IgM, or IgA immune complexes with dye labeled antihuman IgG, antihuman IgM and antihuman IgA antibodies, wherein the dye labeled antihuman IgG, antihuman IgM, and antihuman IgA antibodies are each labeled with a different dye that fluoresces at a non-overlapping emission wavelength, and (e) detecting fluorescence intensities of the dyes to diagnose SARS-CoV-2 infection and/or COVID-19, wherein the fluorescence intensity is proportional to the amount of IgM, IgG, or IgA antibody in the sample, and wherein the amount of IgM, IgG, or IgA antibody in the sample correlates with the time since SARS-CoV-2 infection, (f) evaluating the amount of bound antibody in the duplicate side-by-side substrates to determine avidity, wherein avidity is determined by evaluating the ratio of the IgG level measured in the presence of denaturing agent to the IgG level measured in the absence of denaturing agent, wherein when the ratio is 0.4 to 0.6 or less, or 0.5 or less, the avidity is low; and when the ratio is 0.4 to 0.6 or greater, or 0.5 or greater, the avidity is high; and wherein when the avidity is low, the infection is recent; and when the avidity is high, the infection is old; and (g) treating the subject diagnosed with SARS-CoV-2 infection and/or COVID-19 with a compound or other therapy to mitigate symptoms, prevent spread of SARS-CoV-2 infection, facilitate therapy for others, and/or improve symptoms of COVID-19.

In some embodiments, when the ratio is 0.5 or less, the avidity is low. In some embodiments, when the ratio is 0.5 or greater, the avidity is high.

In some embodiments, the removing the protein denaturing agent comprises rinsing.

In some embodiments, the plasmonic substrate is a plasmonic gold, silver, aluminum, copper, glass, quartz, plastic or nitrocellulose substrate. In some embodiments, the substrate comprises a metallic film arranged discontinuously on the substrate, wherein the metallic film has isolated island areas of between about 100 nm2 and 250,000 $nm^2$ in surface-exposed area, the isolated islands being separated by gaps of about 10 to about 60 nm. In some embodiments, the plasmonic substrate is a plasmonic gold substrate.

In some embodiments, the one or more SARS-CoV-2 antigen is selected from the group consisting of S1, RBD, S2, and nucleocapsid antigen. In some embodiments, the one or more SARS-CoV-2 antigens are SARS-CoV-2 S1 and RBD. In some embodiments, the one or more SARS-CoV-2 antigen is a SARS-CoV-2 antigen variant selected from the group consisting of variants: (i) N501Y; (ii) K417N, E484K, and N501Y; (iii) E484K; K417N; (iv) L452R and E484Q; (v) K417T, E484K, and N501Y; (vi) K417T; (vii) HV69-70 deletion, a Y144 deletion, N501Y, A570D, D614G, P681H, T716I, S982A, and D1118H; (viii) L18F, D80A, D215G, a LAL242-244 deletion, R246I, K417N, E484K, N501Y, D614G, and A701V; (ix) D80A, K417N, E484K, N501Y, D614G, and A701V; (x) L18F, T20N, P26S, D138Y, R190S, K417T, E484K, N501Y, D614G, H655Y, T1027I, and V1176F; and (xi) L18F, T20N, P26S, D138Y, R190S, K417T, E484K, N501Y, D614G, H655Y, T1027I. In some embodiments, the plasmonic substrate further comprises at least one antigen selected from a MERS antigen, and a common cold antigen selected from the group consisting of human coronaviruses consisting of 229E, NL63, OC43, and HKU1.

In another aspect the disclosure provides a method of assessing the efficacy of a SARS-CoV-2 vaccine; the method comprising: (a) obtaining, or having obtained, a biological sample from the subject; (b) contacting the biological sample to one or more SARS-CoV-2 antigens, wherein the one or more SARS-CoV-2 antigens are bound on a plasmonic substrate, and wherein the one or more SARS-CoV-2 antigen specifically bind to one or more IgM, IgG, IgA antibody in the biological sample to form immune complexes, and wherein the plasmonic substrate is present in a multiple well format such that duplicate substrates are located side-by-side, (c) adding a protein denaturing agent to one of the duplicate substrates either prior to or after step (b), to destabilize the immune complexes, followed by a rinse step to remove the protein denaturing agent, thereby removing unbound and low avidity antibodies, (d) contacting the IgG, IgM, or IgA immune complexes with dye labeled antihuman IgG, antihuman IgM and antihuman IgA antibodies, wherein the dye labeled antihuman IgG, antihuman IgM, and antihuman IgA antibodies are each labeled with a different dye that fluoresces at a non-overlapping emission wavelength, and (e) detecting fluorescence intensities of the dyes to diagnose SARS-CoV-2 infection and/or COVID-19, wherein the fluorescence intensity is proportional to the amount of IgM, IgG, or IgA antibody in the sample, and wherein the amount of IgM, IgG, or IgA antibody in the sample indicates the time since SARS-CoV-2 infection, (f) evaluating the amount of bound antibody in the duplicate side-by-side substrates to determine avidity, wherein avidity is determined by evaluating the ratio of the IgG level measured in the presence of denaturing agent to the IgG level measured in the absence of denaturing agent, wherein when the ratio is 0.4 to 0.6 or less, or 0.5 or less, the avidity is low; and when the ratio is 0.4 to 0.6 or greater, or 0.5 or greater, the avidity is high; and wherein when the avidity is low, the vaccine is a low efficacy vaccine; and when the avidity is high, the vaccine is a high efficacy vaccine; and (g) developing, refining, or selecting the high efficacy vaccine for further development or use in immunizing a subject against SARS-CoV-2 infection.

In some embodiments, when the ratio is 0.5 or less, the avidity is low. In some embodiments when the ratio is 0.5 or greater, the avidity is high.

In another aspect the disclosure provides a kit for use in diagnosing or prognosticating SARS-CoV-2 infection and/or COVID-19 in a subject, or for the kit comprising: (a) fluorescence signal enhancing plasmonic gold slides spotted with bound SARS-CoV-2 antigens, (b) dye-labeled detection antibodies, (c) standard controls, (d) diluents, (e) denaturing agents, and (f) instructions for use.

Other features, objects, and advantages will be apparent from the description that follows.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Definitions

Figure 1:
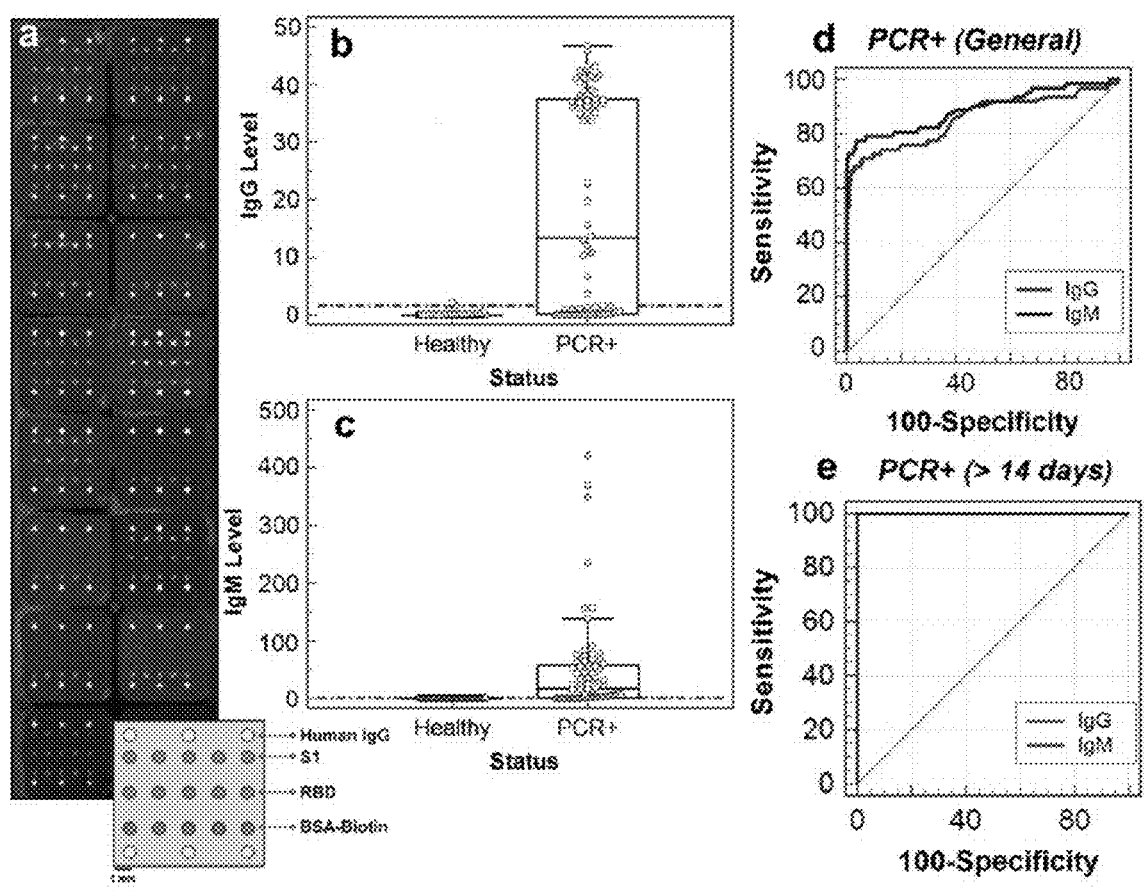
FIG. 1 (a) illustrates an overlay of confocal fluorescence scanned images of IgG (green) and IgM (red) channels acquired after testing 16 serum samples in 16 isolated wells (square-shaped regions). Yellowish-green colored spots correspond to the presence of both IgG and IgM in the sample. The lower right schematic drawing shows the printing layout of S1 (in green) and RBD (in blue) antigens and human IgG control spots (in white) in each well. The BSA-biotin spots (in red) are always labeled by a streptavidin dye in the IgM fluorescence channel to serve as an intrawell signal normalizer. (b) shows box plots of IgG levels detected in PCR-negative COVID-19 or presumptive negative ('Healthy') and PCR-positive ('PCR+') COVID-19 samples with the cutoff indicated as a dashed red line. (c) shows box plots of IgM levels detected in PCR-negative COVID-19 or presumptive negative ('Healthy') and PCR-positive ('PCR+') COVID-19 samples with the cutoff indicated as a dashed red line. (d) ROC curve for pGOLD™ SARS-CoV-2 IgG/IgM assay based on 384 negative and 62 PCR-positive COVID-19 serum, which was used to establish IgG and IgM cutoffs. (e) is a ROC curve for pGOLD™ SARS-CoV-2 IgG/IgM assay based on 384 negative and PCR-positive COVID-19 serum samples collected 15-45 days post symptom onset.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art. As appropriate, procedures involving the use of commercially available kits and reagents are generally carried out in accordance with manufacturer defined protocols and/or parameters unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value ±10%, ±5%, or ±1%. In certain embodiments, where indicated, the term "about" indicates the designated value ±one standard deviation of that value.

The term "combinations thereof" includes every possible combination of elements to which the term refers.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The term "control," "reference level," "reference sample," "control level," "control sample," or grammatically equivalent expressions are used interchangeably herein to refer to a reference sample to which a test sample from a subject is compared.

The term "multiplexed" as used herein, refers to the use and/or testing of multiple biomarkers (analytes) simultaneously in a single assay. Accordingly, a multiplexed assay is capable of testing e.g., both IgM and IgG antibodies in the same patient sample against multiple antigens e.g., SARS-CoV-2 antigens, MERS antigens, common cold antigens, etc., simultaneously.

The terms "patient," "subject," "individual," and the like are used interchangeably herein, and refer to any animal amenable to the methods described herein. In certain non-limiting embodiments, the patient, subject, or individual is a human.

The term "plasmonic" as used herein refers to the generation of collective oscillations of electrons at optical frequencies along metal-dielectric interfaces in the nanometer scale excited by an incident light. The term "plasmonic substrate" as used herein refers to a substrate having "plasmonic properties." The term "plasmonic properties" refers to properties exhibited by surface plasmons, or the collective oscillations of electrical charge on the surfaces of metals which are measurable properties, such as those described e.g. in Nagao et al. *Plasmons in nanoscale and atomic-scale systems*, Sci. Technol. Adv. Mater. 11 (2010) 054506 (12 pp). Plasmonic properties are detectable using plasmonic sensors, such as those used for surface-enhanced IR absorption spectroscopy (SEIRA), surface-enhanced Raman scattering (SERS). Another plasmonic property is plasmon-enhanced fluorescence, described e.g. in Stranik, O., et al. Sensors and Actuators B 107 (2005) 148-153.

The term "islands" or "isolated island areas" is used herein to refer to nanometer-sized metal islands e.g., gold islands, or discontinuous metal nanostructures. The islands may be a variety of shapes and configurations that provide nanometer sized raised areas of material (e.g. gold) separated by gaps without such material. The metal islands form a metallic film, e.g., gold islands that form a nanostructure gold film.

The term "coated" has a meaning as typically understood in the art and refers to binding of antigens to a plasmonic substrate by micro-printing, physisorption, or other known methods.

The term "NIR" means near-infrared, particularly in the sense of NIR fluorescence. The term also means the near-infrared region of the electromagnetic spectrum, typically from 0.6 to 3 μm.

The term "NIR fluorescence enhancement" as used herein refers to an enhancement of near-infrared fluorescent intensity of a fluorophore in proximity to a metal where fluorophores in the excited state undergo near-field interactions with the metal particles to create plasmons. The enhancement results from plasmon-coupling and amplification.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. Antibodies of the present disclosure include e.g., soluble immunoglobulins from any of the IgA, IgG, or IgM iso-types (classes/subtype) as well as anti-human antibodies that bind the IgA, IgG, and/or IgM immunoglobins.

The term "anti-human IgA," "anti-human IgG," or "anti-human IgM" antibody as used herein refers to a polypeptide capable of specifically binding to human IgA antibody, human IgG antibody, or human IgA antibody, respectively, or a fragment thereof. The term "specifically binding" refers to binding to only a target antigen (human IgA, IgG, or IgM or a fragment thereof). The term "specifically binds," as used herein with respect to an antibody, refers to an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some embodiments, specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. Anti-human antibodies against IgA, IgG, or IgM antibodies can be prepared by well-known methods using a purified protein or a suitable fragment derived therefrom as an antigen. A fragment which is suitable as an antigen may be identified by antigenicity determining algorithms well-known in the art. Such fragments may be obtained either from the polypeptide by proteolytic digestion or may be a synthetic peptide. Anti-human antibodies disclosed herein, specifically bind (i.e. does not cross react with other polypeptides or peptides) to the human IgA, IgG, or IgM antibodies. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Kohler and Milstein (1975), Nature 256, 495; and Galfre (1981), Meth. Enzymol. 73, 3, which comprise the fusion of mouse myeloma cells to spleen cells derived from immunized mammals.

The term "antigen" as used herein is defined as a molecule that provokes an immune response. The skilled artisan understands that any macromolecule, including proteins or peptides, can serve as an antigen. Antigens can be derived from recombinant or genomic DNA and can be encoded by a full-length nucleotide sequence of a gene or a fragment thereof. Thus, a skilled artisan will understand that any DNA that comprises a nucleotide sequence or a partial nucleotide sequence encoding a protein that elicits an immune response therefore encodes an "antigen." Moreover, a skilled artisan will understand that an antigen need not be encoded by a "gene" at all. It is readily apparent that an antigen can be generated, synthesized, or can be derived from a biological sample. Such a biological sample can include, but is not limited to a tissue sample, a cell, or a biological fluid.

The term "avidity" as used herein, has meaning as commonly understood in the art and refers to the strength of the antigen-antibody bond after formation of reversible antibody-antigen complexes. Thus, the term "avidity" refers to the combined strength of the antibody-antigen complex.

The term "SARS-CoV-2 antigen" as used herein, refers to a SARS-CoV-2 peptide or protein that elicits and immune response. The term "SARS-CoV-2 antigen" includes "SARS-CoV-2 antigen variants." The term "SARS-CoV-2 antigen variants" or "SARS-CoV-2 variant" as used herein refers to an expressed SARS-CoV-2 protein whose amino acid sequence differs from the "wild-type" reference sequence. The "wild-type" SARS-CoV-2 genome has been sequenced and is known in the art (see e.g., Wu et al. (2020) cell Host & Microbe 27(3): 325-328; Wang, H., et al (2020). Eur J Clin Microbiol Infect Dis 39, 1629-1635). Thus, "SARS-CoV-2 variants" include variants that currently exist, as well as variants that may arise or be discovered in the future. Exemplary SAR-CoV-2 variants include, but are not limited to receptor variants B.1.1.7 which comprises mutation N501Y; B.1.351 which comprises substitution mutations K417N, E484K, and N501Y; B.1.351 which comprises substitution mutations E484K; B.1.351 which comprises substitution mutation K417N; B.1.617 which comprises substitution mutations L452R, and E484Q; P.1 which comprises substitution mutations K417T, E484K, N501Y; P.1 which comprises substitution mutation K417T; B.1.1.7 which comprises a HV69-70 deletion, a Y144 deletion, and substitution mutations N501Y, A570D, D614G, P681H, T716I, S982A, and D1118H; B.1.351 which comprises substitution mutations L18F, D80A, D215G, a LAL242-244 deletion, and substitution mutations R246I, K417N, E484K, N501Y, D614G, and A701V; B.1.351 which comprises substitution mutations D80A, K417N, E484K, N501Y, D614G, and A701V; P.1 which comprises substitution mutations L18F, T20N, P26S, D138Y, R190S, K417T, E484K, N501Y, D614G, H655Y, T1027I, and V1176F; and P.1 which comprises substitution mutations L18F, T20N, P26S, D138Y, R190S, K417T, E484K, N501Y, D614G, H655Y, T1027I.

The term "chemiluminescent immunoassay" is an immunoassay technique where the label, or "indicator" of the analytic reaction, is a luminescent molecule. Chemiluminescent technology is known in the art (see e.g., Luigi Cinquanta, et. al. (2017) Autoimmunity Highlights vol. 8, Article number: 9).

The term "isolated" as used herein means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "sensitivity" as used herein has the meaning commonly understood in the art (see e.g., Fawcett, Tom (2006) Pattern Recognition Letters. 27 (8): 861-874). "Sensitivity" is a statistical measure of how well a binary classification test correctly identifies a condition, and refers to the ability of the analytical method or algorithm to truly determine the individuals that have the disease. Thus, sensitivity is a measure of how well a test can identify true positives. As known in the art (Yerushalmy, J. (1947) Public Health Reports. 62 (2): 1432-39; Fawcett, Tom (2006) supra; Powers, David M W (2011) Journal of Machine Learning Technologies. 2 (1): 37-63), sensitivity measures the proportion of positives that are correctly identified (e.g. the proportion of those who have HCC who are correctly identified as having the condition). Thus, Sensitivity=True Positive/(True Positive+False Negative)×100%.

The term "specificity" as used herein has the meaning commonly understood in the art (see e.g., Fawcett, (2006) supra). "Specificity" is a statistical measure of how well a binary classification test correctly identifies a condition, for example how frequently it correctly classifies a subject having HCC or at elevated risk of developing HCC. "Specificity" measures the proportion of negatives that are correctly identified (e.g. the proportion of those who do not have HCC who are correctly identified as not having HCC). Thus, Specificity=True Negative/(False Positive+True Negative)×100% or 1-false positive rate.

The term "receiver operating characteristic (ROC) curve" refers to a graphical measure of sensitivity (y-axis) vs. 1—specificity (x-axis) for a clinical test, which is known in the art (see e.g., Fawcett, (2006) supra). A measure of the accuracy of a clinical test is the area under the ROC curve value (AUC value). If this area is equal to 1.0 then this test is 100% accurate because both the sensitivity and specificity are 1.0 so there are no false positives and no false negatives. On the other hand a test that cannot discriminate is the diagonal line from 0,0 to 1,1. The ROC area for this line is 0.5. ROC curve areas (AUC-values) are typically between 0.5 and 1.0. Thus, an AUC-value close to 1 (e.g. 0.95) represents a clinical test as that has high sensitivity and specificity and accuracy.

The term "SARS-CoV-2 infection" as used herein refers to a condition wherein a subject has been exposed to the SARS-CoV-2 virus and the virus has entered the body of the subject. In some embodiments, the SARS-CoV-2 has replicated within the body of the subject. In some embodiments, a "SARS-CoV-2 infection" is asymptomatic. In some embodiments, a "SARS-CoV-2 infection" produces disease and a subject having symptomatic COVID-19 exhibits disease symptoms.

The term "recent infection" as used herein refers to an infection acquired less than or equal to approximately six months from the time of testing. The term "old infection" or "remote infection" or "prior infection" as used herein refers to an infection acquired more than about than 6 months prior to testing.

The term "COVID-19" as used herein refers to symptomatic disease resulting from infection by the SARS-CoV-2 virus.

As used herein, the phrase "treating a disorder" or to "treat" or "therapy to improve" a disease or disorder e.g., COVID-19, refers to subjecting a subject to a treatment, e.g., the administration of a drug, such that at least one symptom of the disease as experienced by the subject, is reduced in frequency or severity, or is cured, alleviated, or decreased. Where no curative treatments are available or practical, the phrase, "treating a disorder" or "therapy to improve a disease or disorder" includes recommending quarantine or palliative care.

The term "therapeutically effective amount" refers to the amount of a composition that will elicit a biological or medical response of a tissue, system, or subject that is being treated so as to attenuate, ameliorate, or eliminate one or more symptoms of a condition, disorder, or disease or to cure a condition, disorder, or disease, to delay the onset of or relapse (reoccurrence) of a particular condition, symptom, disorder, or disease, to provide relief from the symptoms of a disorder or disease, or to prevent the onset of a particular condition, symptom, disorder, or disease. Thus, the term "therapeutically effective amount" includes that amount of a composition that, when administered, is sufficient to prevent development of, or alleviate to some extent, one or more of the signs or symptoms of the disorder or disease (e.g., COVID-19) being treated. The therapeutically effective amount will vary depending on the composition, the disease and its severity and the age, weight, etc., of the subject to be treated.

INTRODUCTION

The outbreak and rapid spread of SARS-CoV-2 virus has resulted in a pandemic that has profoundly impacted all people on the planet. Accordingly, highly accurate detection of antibodies for COVID-19 is becoming increasingly indispensable in the fight against the pandemic. It is crucial to aiding diagnosis and assessing infection timing, prevalence, duration of antibody response, and potential immunity.

Thus far, a variety of antibody tests have been developed, but with limited accuracies and capabilities. Accurate and early detection of SARS-CoV-2 is critical to avoid misinterpretations or false positives, unnecessary stress and quarantine, and to prevent controversies and wrong conclusions for surveillance or prevalence studies. Unfortunately however, few if any, assays differentiate antibody subtypes, and none with sufficient (>99.5%) specificity and sensitivity for both IgG and IgM. Furthermore, there is no antibody avidity test for SARS-CoV-2 antibodies. Therefore, current assays lack the ability to measure antibody maturation, and therefore current assays cannot make a determination as to whether a SARS-CoV-2 infection is recent or remote, or is a primary or secondary infection, and cannot be used to assess vaccine efficacy.

Thus, what is needed in the art, are sensitive, accurate, non-invasive tests for SARS-CoV-2 antibodies, that measure antibody avidity and can amongst other things, differentiate primary infection from secondary infection. Such a test could greatly facilitate population-based mass screening for COVID-19.

Accordingly, in at least one aspect, the disclosure provides a single assay method of detecting at least one IgG, IgM, or IgA subtype antibody subtype, or a combination thereof, that binds at least one coronavirus antigen in a biological sample of a subject, the method comprising:
(a) obtaining, or having obtained, the biological sample;
(b) contacting the biological sample to the at least one coronavirus antigen on a substrate wherein the at least one coronavirus antigen binds to one or more IgM, IgA, IgG antibody, or a combination thereof, in the sample and form immune complexes;
(c) detecting the at least one IgG, IgM, or IgA subtype antibody, or a combination thereof, that binds the at least one coronavirus antigen in a biological sample by detecting fluorescence intensities, at different emission wavelengths, from at least one dye labeled to at least one IgG, IgM, or IgA subtype antibody that binds at least one coronavirus antigen;
(d) comparing the detected fluorescence intensities to corresponding fluorescence intensities measured in a control sample;
(e) determining if the subject was infected with SARS-CoV-2 infection and/or had COVID-19 disease.

In some embodiments, the at least one coronavirus antigen are coated at distinct locations on the substrate. In some embodiments, the method comprises using multiplexed analysis of antibodies against a panel of antigens to optimize assay sensitivity and specificity. In some embodiments, the method further comprises combining the determining if the subject was infected with SARS-CoV-2 infection and/or had COVID-19 disease with additional information to diagnosis a SARS-CoV-2 infection. In some embodiments, the method further comprises combining the determining if the subject was infected with SARS-CoV-2 infection and/or had COVID-19 disease with additional information to diagnosis that the subject had COVID-19 disease. In some embodiments, the method further comprises differentiating the subject as having an infection in the acute phase of less than 14 days or convalescent phase of greater than 14 days.

In some embodiments, the substrate is a plasmonic gold substrate. In some embodiments, the substrate is a silver, aluminum, copper, glass, quartz, plastic or nitrocellulose substrate. In some embodiments, the substrate is inside a well of 96-well plate or a 384-well plate.

In some embodiments, the at least one coronavirus antigen is selected from the group consisting of a SARS-CoV-2 S1 subunit, an RBD, a S2 subunit or nucleocapsid protein, SARS-CoV-1 antigens. In some embodiments, the method further comprises coating the substrate with at least one antigen selected from the group consisting of a MERS antigens and a common cold antigen comprising selected from human coronaviruses 229E, NL63, OC43, and HKU1.

In some embodiments, the biological sample is a member selected from the group consisting of human serum, plasma, whole blood, dried blood spot dissolved in buffer solution, and saliva. In some embodiments, the biological sample is saliva.

In some embodiments, the detecting fluorescence intensities, at different emission wavelengths, comprises detecting non-overlapping emission wavelength ranges for IgG, IgM and IgA using three different dye labeled antihuman IgG, antihuman IgM and antihuman IgA, respectively. In some embodiments, the detecting fluorescence intensities, at different emission wavelengths, comprises detecting fluorescence intensities on a plasmonic substrate that enhances fluorescence signals by up to 100 times compared to the fluorescence intensities measured on a non-plasmonic substrate. In some embodiments, the detecting fluorescence intensities, at different emission wavelengths, comprises detecting fluorescence intensities from dyes emitting in the near infrared range including e.g., Cy3, Cy5, CF647, IRdye800, IR820, and iFluo820.

In some embodiments, the method further comprises adding in step (b) a protein denaturing agent at a concentration of 1 to 10 M intended to destabilize immune complexes, for detecting IgG, IgM and IgA levels in the presence of denaturing and destabilizing agent.

In some embodiments, the method further comprises dividing the IgG level measured on each antigen by the IgG level measured to derive avidity of IgG towards the antigen, wherein when the ratio is about 0.5 or less the avidity is low and when the ratio is about 0.5 or greater than the avidity is high, and wherein IgG avidity for antibodies against antigens comprising at least one of a SARS-CoV-2 S1 subunit, an RBD, a S2 subunit or nucleocapsid protein, SARS-CoV-1 antigens, MERS antigens, and a common cold antigen comprising human coronaviruses 229E, NL63, OC43, and HKU1 is measured in a single assay.

In some embodiments, the method further comprises incubating the immune complexes with a protein denaturing agent for a period of about 1 minute to about 60 minutes. In some embodiments, the method further comprises incubating the immune complexes with a protein denaturing agent for a period of about 10 minutes to about 30 minutes. In some embodiments, the incubating is followed by a rinse step to remove the protein denaturing agent, and unbound and low avidity antibodies. In some embodiments, the protein denaturing agent is selected from at least one of urea, formamide, guanidine, sodium salicylate, dimethyl sulfoxide, and propylene glycol. In some embodiments, the denaturing agent comprises urea. In some embodiments, the protein denaturing agent comprises formamide.

In some embodiments, the avidity of IgG towards SARS-CoV-2 S1, SARS-CoV-2 RBD, SARS-CoV-2 S2, SARS-CoV-2 nucleocapsid, SARS-CoV-1 antigens, MERS antigens and antigens of other human coronaviruses 229E, NL63, OC43, and HKU1 are measured in a multiplexed manner to assess a recent or remote infection or re-infection. In some embodiments, the virus antigens comprise recombinant viral antigens or viral lysates.

In some embodiments, the sample is saliva from an individual diluted by 2-10 times in a buffer solution containing biological additives. In some embodiments, the sample is saliva from an individual diluted by 2-4 times in a buffer solution containing biological additives. In some embodiments, the diluted saliva is centrifuged to remove aggregates and retain the supernatant for antibody testing.

In some embodiments, the sample is a dried blood spot on a nitrocellulose card from an individual dissolved in a buffer solution. In some embodiments, the dried blood spot is formed by venous blood. In some embodiments, the dried blood spot is formed by capillary blood or finger prick blood. In some embodiments, the dried blood spot is collected in a local or remote lab, office, or home and mailed to a CLIA lab for testing antibodies against SARS-CoV-2 and other coronaviruses. Clinical Laboratory Improvement Amendments (CLIA) regulate laboratory testing and require clinical laboratories to be certified by the Center for Medicare and Medicaid Services (CMS) before they can accept human samples for diagnostic testing.

In some embodiments, the method comprises a blocking step prior to steps (c)-(g) to reduce non-specific binding. In some embodiments, background subtraction is used after steps (c)-(g) to analyze the antibody signal bound to antigens.

In some embodiments, the saliva is collected in a local or remote location including lab, office or home and mailed to a CLIA lab for testing antibodies against coronaviruses.

In some embodiments, the substrate is plasmonic-active. In some embodiments, the substrate comprises a nanostructured metallic gold film arranged on the substrate in a manner that enhances near infrared fluorescence by 10-fold to 100-fold or more relative to the substrate without the metallic film, allowing optimized sensitivity of SARS-CoV-2 assays. The metal particle dimensions can be tailored in order to tune the plasmon resonance wavelength to match the spectral absorption of the fluorophore. Thus, in some embodiments, the substrate comprises a metallic film arranged discontinuously on the substrate wherein the metallic film has isolated island areas of between about 100 $nm^2$ and 250,000 $nm^2$ in surface-exposed area, the isolated islands being separated by gaps of about 10 to about 60 nm. In some embodiments, the metallic film comprises a metal selected from at least one of gold and silver.

In another aspect, the disclosure provides a method of diagnosing recent versus remote SARS-CoV-2 viral infection by evaluating IgG avidity towards S1; wherein when the avidity is low, the infection is recent; and wherein when the avidity is high, the infection is an old infection, wherein recent is defined as less than or equal to approximately 6 months, and wherein an old infection is when the infection occurred longer than 6 months prior.

In some embodiments, the S1 virus antigen comprises recombinant viral antigens or viral lysates.

In some embodiments, the avidity test for assessing coronavirus infection timing is performed by using a microarray platform based on plasmonic and non-plasmonic substrates comprising at least one of metals, glass, quartz and nitrocellulose, ELISA, digital ELISA, lateral flow assays, Luminex, chemiluminescence assays, bead-based fluorescence assays, and electro-chemical luminescence assays.

In some embodiments, the substrate is plasmonic-active. In some embodiments, the substrate comprises a metallic film arranged on the substrate in a manner that enhances near infrared fluorescence by 2-fold to 100-fold or more relative to the substrate without the metallic film. In some embodiments, the metallic film comprises a metal selected from at least one of gold and silver. In some embodiments, the substrate comprises a metallic film arranged discontinuously on the substrate wherein the metallic film has isolated island areas of between about 100 nm$^2$ and 250,000 nm$^2$ in surface-exposed area, and the isolated islands are separated by gaps of about 10 to about 60 nm.

In another aspect, the disclosure provides a method of diagnosing recent infection and remote infection of SARS-CoV-2 by evaluating multiplexed IgG avidity towards at least one of S1, RBD, S2 or nucleocapsid antigen; wherein when the avidity is low, the infection is recent; and wherein when the avidity is high, the infection is old; wherein recent is defined as less than or equal to approximately 6 months; and wherein an old infection is when an infection occurred longer than 6 months prior. In some embodiments, the virus antigens comprise recombinant viral antigens or viral lysates.

In some embodiments, the avidity test for assessing coronavirus infection timing is performed by using a microarray platform based on plasmonic and non-plasmonic substrates comprising at least one of metals, glass, quartz and nitrocellulose, ELISA, digital ELISA, lateral flow assays, Luminex, chemiluminescence assays, bead-based fluorescence assays, and electro-chemical luminescence assays. In some embodiments, the substrate is plasmonic-active. Thus, in some embodiments, the substrate comprises a metallic film arranged on the substrate in a manner that enhances near infrared fluorescence by 2-fold to 100-fold or more relative to the substrate without the metallic film. In some embodiments, the metallic film comprises a metal selected from at least one of gold and silver. In some embodiments, the substrate comprises a metallic film arranged discontinuously on the substrate wherein the metallic film has isolated island areas of between about 100 nm$^2$ and 250,000 nm$^2$ in surface-exposed area, the isolated islands being separated by gaps of about 10 to about 60 nm.

In one aspect, the disclosure provides a method of diagnosing recent infection and remote infection of SARS-CoV-1, MERS and other human coronaviruses 229E, NL63, OC43, and HKU1 by evaluating multiplexed IgG avidity towards their respective antigens, or all of the avidities combined; wherein when the avidity is low, the infection is recent; and wherein when the avidity is high, the infection is old, wherein the recent infection is less than or equal to approximately six months; and wherein the old infection is when the infection occurred longer than six months prior. In some embodiments, the virus antigens comprise recombinant viral antigens or viral lysates.

In some embodiments, the avidity test for assessing coronavirus infection timing is performed by using a microarray platform based on plasmonic and non-plasmonic substrates comprising at least one of metals, glass, quartz and nitrocellulose, ELISA, digital ELISA, lateral flow assays, Luminex, chemiluminescence assays, bead-based fluorescence assays, and electro-chemical luminescence assays. In some embodiments, the substrate is plasmonic-active. In some embodiments, the substrate comprises a metallic film arranged on the substrate in a manner that enhances near infrared fluorescence by 2-fold to 100-fold or more relative to the substrate without the metallic film. In some embodiments, the metallic film comprises a metal selected from at least one of gold and silver. In some embodiments, the substrate comprises a metallic film arranged discontinuously on the substrate wherein the metallic film has isolated island areas of between about 100 nm$^2$ and 250,000 nm$^2$ in surface-exposed area, the isolated islands being separated by gaps of about 10 to about 60 nm.

In another aspect, the disclosure provides a method of diagnosing a primary and/or secondary SARS-CoV-2, SARS-CoV-1, MERS or other human coronaviruses infection or re-infection in a subject, the method comprising:

(a) detecting IgG, IgM and IgA against one or multiple antigens in biological fluid (serum, plasma, blood, dry blood spots, saliva) of the subject in a single assay;

(b) measuring IgG avidity towards the viral antigens in a single assay;

(c) diagnosing the subject with the primary viral infection upon detecting one or more of IgA, IgM and IgG bound to one or more viral antigens accompanied by low IgG avidity; and (d) diagnosing the subject with the secondary viral infection upon detecting high IgG and IgG avidity to one or more viral antigens corresponding to the coronaviruses.

In some embodiments, the virus antigens comprise recombinant viral antigens or viral lysates.

In some embodiments, the diagnosing is performed by using a microarray platform based on plasmonic and non-plasmonic substrates comprising at least one of metals, glass, quartz and nitrocellulose, ELISA, digital ELISA, lateral flow assays, Luminex, chemiluminescence assays, bead-based fluorescence assays, and electro-chemical luminescence assays or a combination thereof.

In some embodiments, the substrate is plasmonic-active. In some embodiments, the substrate comprises a metallic film arranged on the substrate in a manner that enhances near infrared fluorescence by 2-fold to 100-fold or more relative to the substrate without the metallic film. In some embodiments, the metallic film comprises a metal selected from at least one of gold and silver. In some embodiments, the substrate comprises a metallic film arranged discontinuously on the substrate wherein the metallic film has isolated island areas of between about 100 nm$^2$ and 250,000 nm$^2$ in surface-exposed area, the isolated islands being separated by gaps of about 10 to about 60 nm.

General Methods

This disclosure utilizes techniques in the field of recombinant genetics. Basic texts disclosing the general methods and terms in molecular biology and genetics include e.g., Sambrook et al., *Molecular Cloning, a Laboratory Manual*, Cold Spring Harbor Press 4th edition (Cold Spring Harbor, N.Y. 2012); *Current Protocols in Molecular Biology* Volumes 1-3, John Wiley & Sons, Inc. (1994-1998) and periodic updates. This disclosure also utilizes techniques in the field of biochemistry. Basic texts disclosing the general methods and terms in biochemistry include e.g., Lehninger *Principles of Biochemistry* sixth edition, David L. Nelson and Michael M. Cox eds. W.H. Freeman (2012). Basic texts disclosing the general methods and terms in immunology include

*Janeway's Immunobiology* (Ninth Edition) by Kenneth M. Murphy and Casey Weaver (2017) Garland Science; *Fundamental Immunology* (Seventh Edition) by William E. Paul (2013) Lippincott, Williams and Wilkins; and Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426. Basic texts disclosing the general methods and terms of plasmonics include e.g., Molecular Plasmonics: Theory and Applications, Volodymyr I. Chegel, Andrii M. Lopatynskyi eds. (2021) CRS press; Introduction to metal-Nanoparticle Plasmonics, Matthew Pelton and Garnett Bryant eds. (2013) Wiley.

Sample Collection and Data Generation

Saliva samples can be collected from patients using any method known in the art e.g., using through a simple spitting method, or through a kit such as e.g. Salivette kits, which are chewable cotton swabs which absorb saliva.

Antigen Preparation and Antibody Assays

Full length or fragments of spike protein and nucleocapsid antigens can be prepared by any method known in the art or purchased from commercial vendors such as e.g., Sino Biological). Various methods, well known in the art, may be used to produce proteins and peptides in bacteria and other microorganisms. The skilled artisan is well aware of the genetic elements that must be present on an expression construct/vector in order to successfully transform, select, and propagate an expression construct comprising a peptide based antigen in host cells. Techniques for manipulation of nucleic acids encoding SARS-CoV-2 antigens such as subcloning nucleic acid sequences into expression vectors, labeling probes, DNA hybridization, and the like are described generally in Sambrook, et al.; *Current Protocols in Molecular Biology*, supra.

Illustrative SARS-CoV-2 antigens include, but are not limited to wild-type S1, RBD, S2, and nucleocapsid antigens and non-wild-type variants thereof. Thus, in some embodiments, SARS-CoV-2 antigens include variant antigens such as those found in e.g., the UK variant B.1.1.7 (N501Y), the Brazil variant P.1 (K417T, E484K, N501Y; or K417T), the South Africa variant B.1.351 (K417N, E484K, N501Y; or E484K), the India variant B.1.617 (L452R, E484Q) and other variants as may arise.

Anti-human IgG, IgM, and IgA antibodies can be purchased from a manufacturer such as e.g., Gentaur, or may be prepared by methods well known in the art. Methods for the preparation of anti-human antibodies can be found e.g., in Antibodies: A Laboratory Manual, supra.

The present disclosure provides assays for SARS-CoV-2 antibodies in a subject that, due to their sensitivity and dynamic range, permit early detection, and which can be used to detect and distinguish recent and remote infection, in the same assay. Typically, as disclosed herein, SARS-CoV-2 antigens are applied to a substrate e.g., a plasmonically active substrate, and a biological sample from a patient is applied to the substrate. If present, antibodies in the patient sample bind the antigens and in subsequent steps the bound antibodies are detected. Detection of bound antibodies utilizes fluorescently labeled anti-human antibodies directed toward human IgG, human IgM, and human IgA antibodies. The florescent label is then detected using appropriate instrumentation e.g., utilizing MidaScan™/MidaScan-IR™ scanners or other existing fluorescence based microplate readers. Fluorescense signal and intensity at specific antigen spots correlates to the amount of specific antibody isotypes present against the corresponding antigen. The methods disclosed herein have sufficient sensitivity and dynamic range that they permit a multiplex antibody determination which, in some embodiments, may be used to determine the timing of an infection (recent or remote) by measuring antibody avidity and/or if a subject is acutely infected by IgM measurement.

Plasmonic Substrates and pGOLD™

Plasmonic substrates are known in the art (see e.g., Aslan, K. et al. (2005) Metal-.Curr. Opin. Biotechnol. 16, 55-62). In particular, plasmonic gold substrates (see e.g., U.S. Pat. Nos. 9,823,246, and 10,088,478) can enhance protein detection up to 100-fold as compared to non-plasmonic substrates, thus extending the dynamic range of protein detection by three orders of magnitude over other known methods (see e.g., Tabakman, S. M., et al. (2011) Nature Communications 2: 466). In some embodiments, SARS-CoV-2 antibody assays utilizing plasmonic gold substrates are used in fluorescence and Raman based assays.

Synthetic protocols and versatile fabrication methods allow the size, shape, and composition of plasmonic gold nanoparticles (AuNPs), to be tailored for specific applications (see e.g., Nafeesa Sarfraz, N., and Khan, I. (2021) Chemistry—An Asian Journal Vol. 16 (7):720-742). Therefore, in some embodiments, the substrate comprises a plasmonic-active metallic film arranged on glass or other substrate (e.g., silver, aluminum, copper, glass, quartz, plastic, nitrocellulose substrate, etc.) in a manner that enhances near infrared fluorescence by 2-fold to 100-fold or more relative to the substrate without the metallic film. In some embodiments, the substrate comprises a plasmonic-active metallic film arranged on glass or other substrate in a manner that enhances near infrared fluorescence by 10-fold to 100-fold or more relative to the substrate without the metallic film.

Therefore, in some embodiments, the substrate comprises a metallic film arranged discontinuously on the substrate wherein the metallic film has isolated island areas of between about 100 nm$^2$ and 250,000 nm$^2$ in surface-exposed area, the isolated islands being separated by gaps of about 10 to about 60 nm. In some embodiments, the metallic film comprises a metal selected from gold, silver, and combinations thereof.

In some embodiments, dye labeled antihuman IgG, antihuman IgM and antihuman IgA antibodies are labeled with an organic dye wherein the label emits in the 500-1000 nm range. In some embodiments, the plasmonic properties of the film comprise a NIR fluorescence enhancement (NIR-FE) activity. Thus, in some embodiments, the label emits in the near infrared (NIR), including the NIR range of 650-900 nm. In some embodiments, the dye is selected from Cy3, Cy5, CF647, IRdye800, IR820, and iFluo820.

In in some embodiments, the different anti-human antibodies (e.g., IgG, IgM, IgA) are labeled with different dyes that emit with non-overlapping wavelengths in the 500-1000 nm range.

Antibody Avidity Assays

In some aspects the disclosure provides methods for detecting IgG, IgM, and IgG avidity against SARS-CoV-2 spike proteins S1 subunit and RBD in human serum and saliva. Thus, the disclosure provides methods of diagnosing or prognosticating recent or remote SARS-CoV-2 infection in a subject, wherein the subject was recently infected, remotely infected, or recently and remotely infected. Methods for analyzing avidity also are also useful for assessing vaccine efficacy and thus can be used to guide vaccine development. For example, a better, more effective vaccine would elicit higher Ab levels and the Abs will have higher avidity.

Accordingly, the disclosure provides methods for measuring antibody avidity. In general, antibody avidity assays are conducted by measuring antibody binding under conditions favorable for binding and under denaturing conditions and evaluating the ratio of the antibody level measured in the presence of denaturing agent to the antibody level measured in the absence of denaturing agent. A ratio is between about 0.4-0.6, preferably 0.5 or less, indicates low avidity; and a ratio of 0.5 or greater, indicates high avidity.

Denaturing agent can be added together with a biological sample to one or more SARS-CoV-2 antigens at the time that the biological sample is contacted to one or more SARS-CoV-2 antigens, or can be added after the biological sample is contacted to one or more SARS-CoV-2 antigens. Suitable denaturing agents include, but are not limited to urea, formamide, guanidine, sodium salicylate, dimethyl sulfoxide, propylene glycol, and combinations thereof. Typical concentrations of denaturing agent are typically between about 1M to 10M. In some embodiments, the denaturing agent is urea at a concentration of 6M.

Antibody affinity correlates with timing and duration of infection and quality of immune response. Thus, antibody avidity can be used for amongst other things, diagnosing or prognosticating recent or remote SARS-CoV-2 infection in a subject, or can be useful for assessing vaccine efficacy and thus can guide vaccine development. A better vaccine would elicit higher Ab levels and the Abs will have higher avidity.

Compounds and Therapies

The methods disclosed herein can be a factor in determining if a patient should be treated for COVID-19 or not, or can be taken into consideration when deciding what follow-up tests should be done, defining the response to therapies, monitoring any possible recurrences of COVID-19, and identifying new therapeutic targets.

A subject diagnosed as having COVID-19 or as having been infected with SARS-CoV-2 may be treated by any known method in the art.

In some embodiments, a subject diagnosed as having COVID-19 is treated by administering therapeutically effective amount of Remdesivir (e.g. Veklury® see e.g., Beigel J H, et al. (2020) N Engl J Med. 383(19):1813-1826) or a compound such as that disclosed in U.S. Pat. Nos. 10,905, 698, 10,987,329, or 10,980,756.

In other embodiments, a subject diagnosed as having COVID-19 is treated by administering therapeutically effective amount of an anti-SARS-CoV-2 antibody cocktail such as REGEN-COV™ (casirivimab with imdevimab). In some embodiments, REGEN-COV™ is administered early in a SARS-CoV-2 infection. In other embodiments, a subject diagnosed as having COVID-19 is treated with palliative therapy.

In some embodiments, a subject with past infection who has immunity e.g., a subject having high avidity SARS-CoV-2 antibodies, may be advised that they can safely work in essential settings such as health care, public safety and the service industry. They also can be advised that they can safely work in "non-essential" settings with less need for extreme personal protection.

Alternatively, a subject with past infection who has immunity and high avidity SARS-CoV-2 specific antibodies, can be advised to donate convalescent plasma which can be used to treat other individuals who are experiencing COVID-19, thus preventing severe COVID complications for those other individuals.

Because the methods disclosed herein can detect very early infection (through the ability to accurately and specifically identify the IgM) a person having asymptomatic or pre-symptomatic infection can be advised to seek early treatment e.g., by administration of REGEN-COV™, and/or to engage in immediate isolation or quarantine to prevent spread.

Furthermore, symptomatic individuals can be notified if their symptoms are COVID-related and if not COVID, then they can be advised what other virus they might have and appropriate care for the symptoms can be recommended.

Kits

In one aspect, provided herein are kits useful for diagnosing or prognosticating SARS-CoV-2 infection and/or COVID-19 in a subject. Kits typically comprise fluorescence signal enhancing plasmonic gold slides, spotted with bound SARS-CoV-2 antigens, dye-labeled detection antibodies, standard controls, diluents, denaturing agents, and instructions for use.

EXAMPLE

The following Example illustrates development and use of a semi-quantitative assay utilizing a nanostructured plasmonic gold (pGOLD™) platform to detect IgG, IgM, and IgA avidity against SARS-CoV-2 spike proteins S1 subunit and receptor-binding domain (RBD) in human serum and saliva.

The pGOLD™ substrate was prepared by methods known in the art (see e.g., U.S. Pat. No. 9,823,246) and was comprised of nanoscale gold islands with abundant nanogaps, affording near-infrared (NIR) fluorescence enhancement by up to ~100-fold owing to plasmonic resonance and local electric field enhancements. The greatly increased NIR signal-to-background ratio on pGOLD™ allowed multiplexed detection of panels of biological analytes over wide dynamic ranges.

Fabricated arrays of SARS-CoV-2 spike protein S1 subunit and RBD antigen spots by micro-printing/physisorption on a pGOLD™ slide in a microarray format were prepared (see FIG. 1(a)), for capturing IgG and IgM antibodies in a sample, followed by labeling of the captured antibodies with anti-human IgG-IRDye800 and anti-human IgM-CF647 dye. The pGOLD™ biochip was imaged by a confocal microscopy scanner in the red and NIR channels.

The IgG and IgM antibodies bound to each antigen spot (see FIG. 1(a)) were analyzed through the fluorescence intensities of IRDye800 and CF647 dye, respectively.

Figure 6:
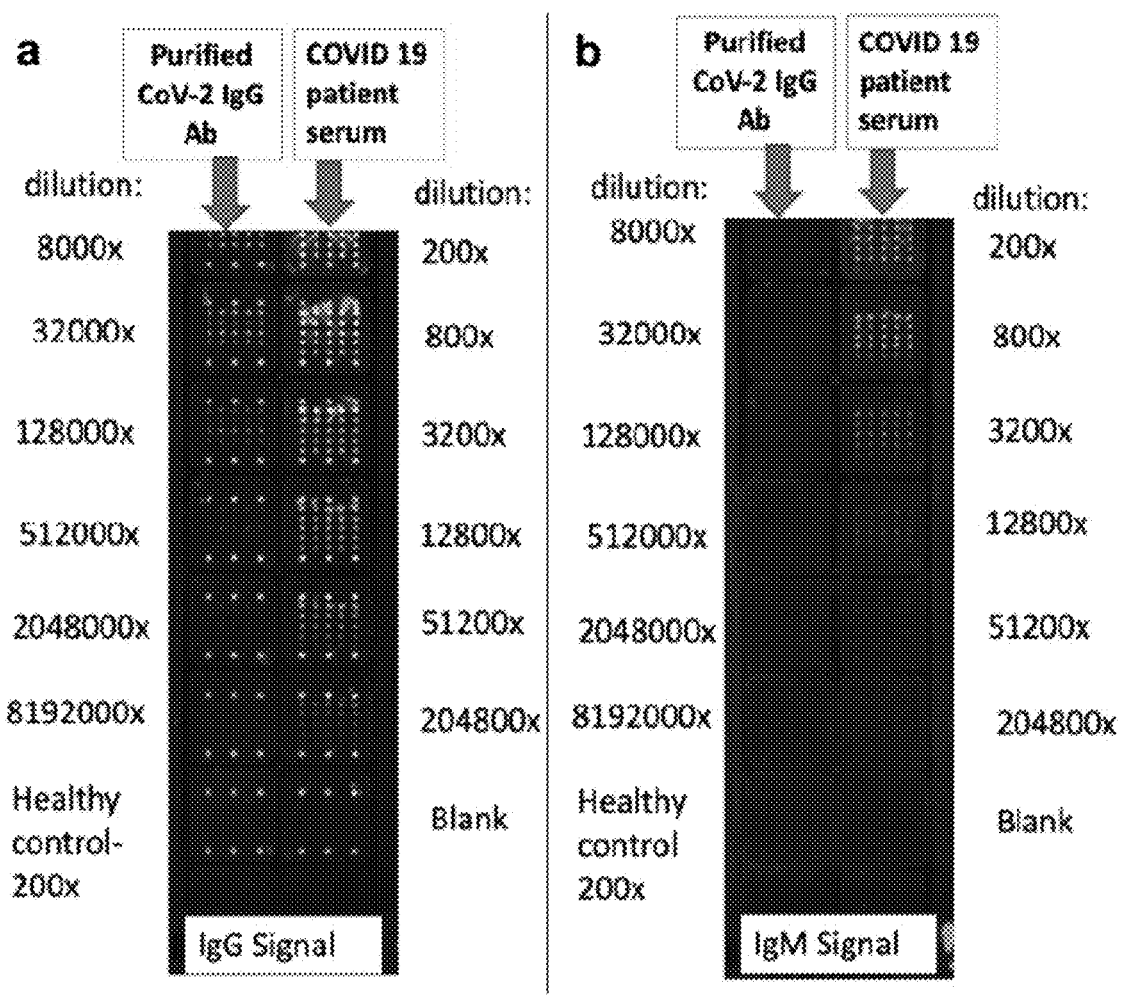
FIG. 6 (a) is a NIR fluorescence image of a pGOLD™ biochip (7.5 cm×2.5 cm) showing SARS-CoV-2 IgG signals labeled by anti-human IgG-IRDye800 of a serially-diluted, purified IgG antibody solution (left column) and a serially-diluted, PCR-confirmed COVID-19 patient serum (right column). (b) is a NIR fluorescence image of SARS-CoV-2 IgM signals labeled by anti-human IgM-IRDye800 of the serially-diluted, purified IgG antibody (left column) and PCR-confirmed COVID-19 patient serum sample (right column). Each sample dilution was assayed in identical square wells with SARS-CoV-2 antigens S1 and RBD prepared at 5× and 10× and printed in 4 rows with 5 spots each. The top and bottom rows in each well were printed with human IgG as control spots.
Figure 7:
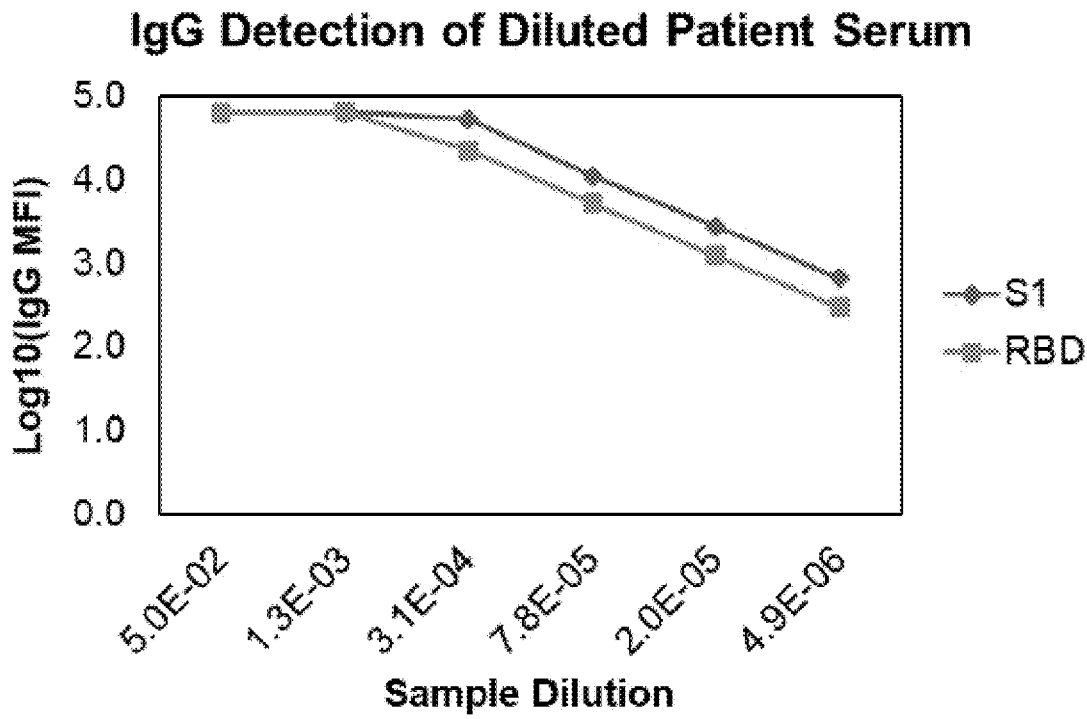
FIG. 7 illustrates log 10 of the IgG median fluorescence intensity (MFI) readings (top) and IgM MFI readings (bottom) of a serially-diluted, PCR-confirmed COVID-19 patient serum against SARS-CoV-2 S1 and RBD antigens. A clear IgG signal was seen up to a dilution of 4.9e-06 and a clear IgM signal up to a dilution of 7.8e-05. The IgG signal was saturated at dilutions of 5.0e-02 and 1.3e-03.
Figure 7:
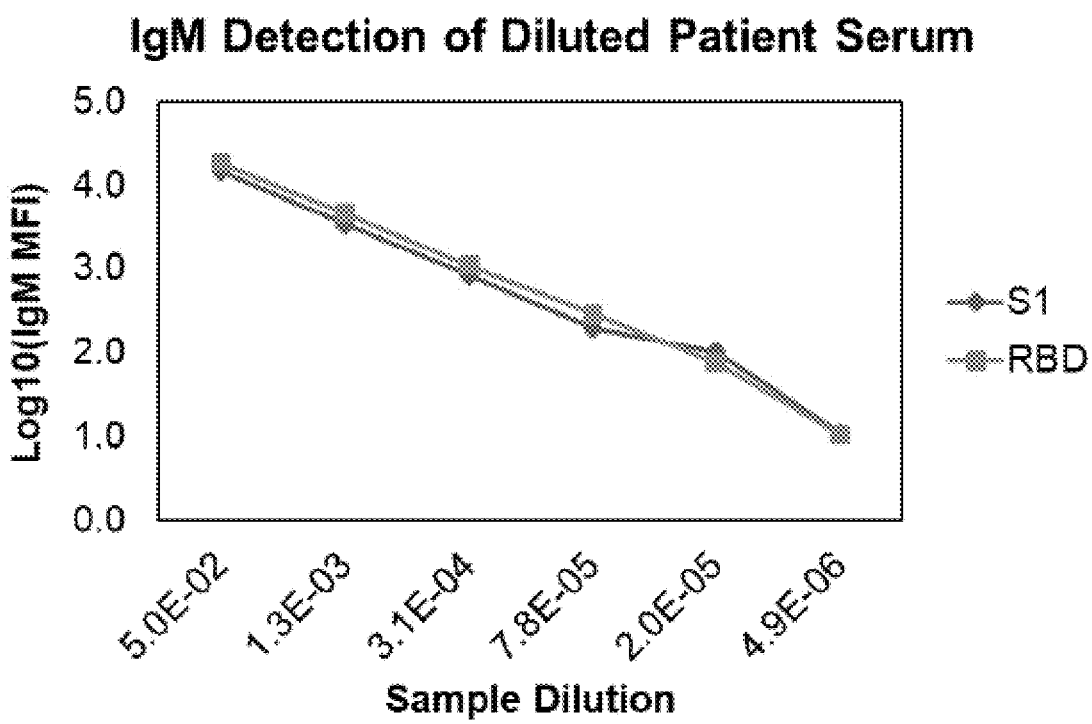

Dilution of a pure humanized SARS-CoV-2 IgG antibody solution over 4 orders of magnitude led to signal changes by ~4 logs, giving an estimated antibody detection limit of ~1.6 ng/mL (See FIGS. 6 and 7). A PCR-confirmed COVID-19 positive patient sample was diluted by up to 105 times, and antibody signals were still well above background noise across all dilutions (See FIGS. 6 and 7). These results suggested high analytical sensitivity and wide dynamic range of the multiplexed pGOLD™ assay.

Specificity of Serum Antibody Binding to pGOLD™ Bound SARS-CoV-2 Antigens

SARS-CoV-2 antibodies were detected on the pGOLD™ assay in human serum samples. Antibodies against the S1 antigen (see FIG. 1(a)) were tested. To determine specificity, a total of 384 negative and presumptive negative samples were tested including 33 from PCR-confirmed COVID-19 negative individuals, 311 pre-pandemic samples collected in 2017-2019, and 40 healthy control samples acquired prior to the COVID-19 outbreak. Also obtained was a set of sera from 62 PCR-confirmed COVID-19 patients (but without information given regarding the number of days between disease symptom onset to sample collection).

The ROC (receiver operating characteristics) curve analysis was performed based on the pGOLD™ assay results for the 384 negative and 62 positive samples (see FIG. 1(d)). The cutoff values were determined under the criteria of >99.5% specificity while maximizing the sensitivity for detecting both IgG and IgM in the sera of COVID-19 patients (see FIGS. 1(b) and 1(c)). Under this condition, only one serum sample from the 384 presumptive negative set was found to be false positive.

Assay specificity and potential for cross-reactivity, or lack thereof, were tested on 70 pre-pandemic samples collected from patients with various diseases, including common colds/other coronaviruses, influenza, autoimmune disease, HBV, HCV, and HIV (see Table 1). All of the samples were found negative in IgG and IgM against SARS-CoV-2. Accordingly, there is near zero cross-reactivity (see FIGS. 2(c) and 2(d)).

Figure 2:
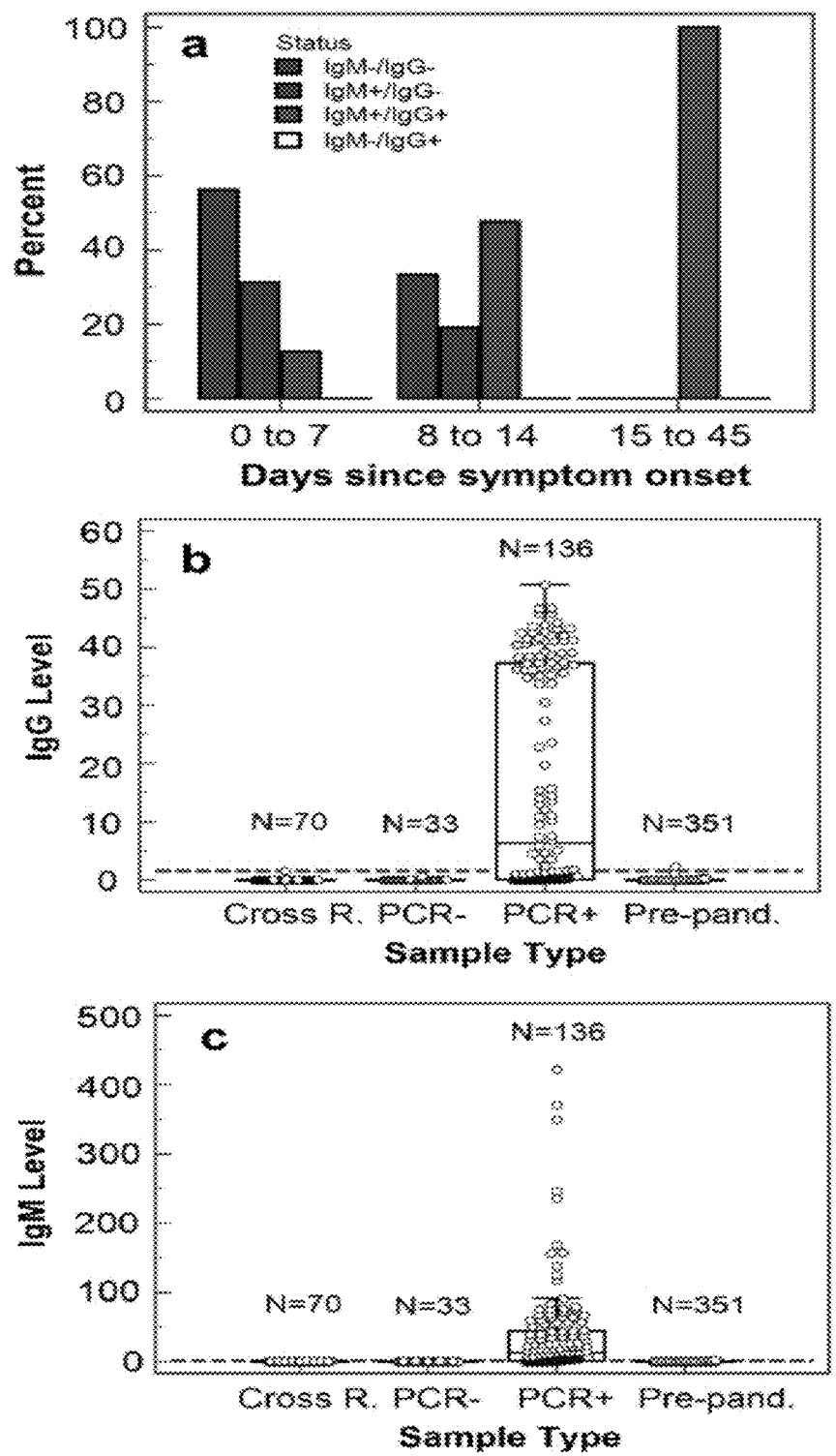
FIG. 2 (a) illustrates percentages of samples with IgG/IgM antibody status combinations according to days from symptom onset to sample collection date in a range from 0-7, 8-14, and 15-45 days. (b) are box plots of IgG levels detected in four groups of serum samples indicated on the x-axis with the cutoff displayed as a dashed red line. 'PCR+' denotes serum samples from patients who tested positive by PCR for COVID-19 and 'PCR−' denotes those who tested negative. 'Pre-pand.' corresponds to pre-pandemic collected samples. 'Cross R.' corresponds to samples from patients with other diseases for cross-reactivity evaluation. (c) are box plots of IgM levels detected in four groups of serum samples indicated on the x-axis with the cutoff displayed as a dashed red line. 'PCR+' denotes serum samples from patients who tested positive by PCR for COVID-19 and 'PCR−' denotes those who tested negative. 'Pre-pand.' corresponds to pre-pandemic collected samples. 'Cross R.' corresponds to samples from patients with other diseases for cross-reactivity evaluation.

All together with a total of 454 pre-pandemic presumptive and PCR-confirmed negative samples (see FIGS. 2(c) and 2(d) and Table 2), only one sample was false positive in IgG and IgM, resulting in an overall specificity of 99.78% for both antibody isotypes.

TABLE 1

Shows cross-reactivity evaluation study conducted for the pGOLD SARS-CoV-2 IgG/IgM assay on the S1 antigen, testing 70 serum samples collected from patients with various diseases. None of the samples tested were positive for either IgG or IgM.

| Disease Type | Reference Method | Numbers of Samples | Nirmidas pGOLD SARS-CoV-2 IgG/IgM assay (S1) | | | |
|---|---|---|---|---|---|---|
| | | | IgM POS | IgM NEG | IgG POS | IgM NEG |
| Coronavirus 229E | BioFire PCR | 1 | 0 | 1 | 0 | 1 |
| Coronavirus NL63 | BioFire PCR | 1 | 0 | 1 | 0 | 1 |
| Coronavirus OC43 | BioFire PCR | 1 | 0 | 1 | 0 | 1 |
| FluA/FluB | ELISA | 5 | 0 | 5 | 0 | 5 |
| FluA | ELISA | 3 | 0 | 3 | 0 | 3 |
| ANA | BioPlex 2200 antibody test | 13 | 0 | 13 | 0 | 13 |
| HBV (AcHBs) | Diasorin Liaison XL | 5 | 0 | 5 | 0 | 5 |
| Haemophilus Influenzae | BioFire PCR | 1 | 0 | 1 | 0 | 1 |
| Rheumatoid Factor | ELISA | 1 | 0 | 1 | 0 | 1 |
| RSV | PCR | 8 | 0 | 8 | 0 | 8 |
| Zika and Dengue IgG | Euroimmune IgG | 8 | 0 | 8 | 0 | 8 |
| Zika IgG/IgM | Euroimmune IgG/InBios IgM | 5 | 0 | 5 | 0 | 5 |
| CHIKV IgG | Euroimmune IgG | 2 | 0 | 2 | 0 | 2 |
| HCV | Antibody test | 6 | 0 | 6 | 0 | 6 |
| HIV | Antibody test | 10 | 0 | 10 | 0 | 10 |
| Total | | 70 | 0 | 70 | 0 | 70 |

TABLE 2

Shows negative agreement of pGOLD SARS-CoV-2 IgG/IgM assay against the S1 antigen for specificity using a total of 454 PCR-negative and pre-pandemic cross-reactive or healthy control ("presumptive negative") samples.

| Number of Samples | Origin | Sample description | pGOLD IgG Results for negative and presumptive negative samples IgG NEG | pGOLD IgM Results for negative and presumptive negative samples IgM NEG |
|---|---|---|---|---|
| 33 | 4 from CDPH and 29 from Loma Linda Medical Center | Confirmed PCR- negative for COVID-19 | 33 | 33 |
| 40 | From Arizona State University Health Services | Pre-pandemic. Samples used as healthy control for projects prior to COVID-19 outbreak | 40 | 40 |

TABLE 2-continued

Shows negative agreement of pGOLD SARS-CoV-2 IgG/IgM assay against the S1 antigen for specificity using a total of 454 PCR-negative and pre-pandemic cross-reactive or healthy control ("presumptive negative") samples.

| Number of Samples | Origin | Sample description | pGOLD IgG Results for negative and presumptive negative samples IgG NEG | pGOLD IgM Results for negative and presumptive negative samples IgM NEG |
|---|---|---|---|---|
| 311 | JSRLSD at the Palo Alto Medical Foundation | Pre-pandemic (collected between 2017 to 2019) | 310 | 310 |
| 70 | Pre-pandemic samples for cross-reactivity evaluation | Pre-pandemic samples for cross-reactivity evaluation | 70 | 70 |
| Specificity Total 95% CI: | | | 453/454 = 99.78% 98.76%-99.96% | 453/454 = 99.78% 98.76%-99.96% |

Sensitivity pGOLD™ SARS-CoV-2 Antibody Assay at Various Times Post Infection

For the 62 PCR-confirmed COVID-19 patient samples collected without days since symptom onset data (see FIG. 1(a)), the sensitivity of the pGOLD™ assay was 51.61% for IgG and 70.97% for IgM (see FIG. 1(d)), suggesting a substantial fraction of the samples was collected in the early stage (<14 days) of SARS-CoV-2 infection prior to the development of antibodies.

To investigate the immune response and sensitivity of our pGOLD™ SARS-CoV-2 antibody assay at various times post infection, an independent set of sera was measured from 70 PCR-confirmed COVID-19 patients collected between 0-45 days post symptom onset. Assessment of antibody status in the second set of samples was performed using the cutoffs generated with the first sample set. Based on the days of symptom onset, PCR-positive patients were divided into three groups: I (0-7 days), II (8-14 days) and III (>14 days). It was found that the positive rate for IgM in each group (I, II, III) was 43.75%, 66.67%, and 100%, respectively (see Table 3). The positive rate for IgG in each group (I, II, III) was 12.5%, 47.62%, and 100%, respectively (see Table 3). The results indicate a high positivity rate of IgM over IgG initially (Group I) to both IgG and IgM antibodies detected in all patients at a late stage post infection (Group III). Table 3 Summary of pGOLD SARS-CoV-2 IgG/IgM assay results against the S1 antigen for 70 samples collected from PCR-positive COVID-19 patients at 0 to 7 (Group I), 8 to 14 (Group II), and 15 to 45 (Group III) days since symptom onset.

| Days since symptom onset | Number of Samples | # IgG Positive | # IgM Positive | # Antibody Positive | % IgG Positive | % IgM Positive | % Antibody Positive |
|---|---|---|---|---|---|---|---|
| 0 to 7 | 16 | 2 | 7 | 7 | 12.50% | 43.75% | 43.75% |
| 8 to 14 | 21 | 10 | 14 | 14 | 47.62% | 66.67% | 66.67% |
| 15 to 45 | 33 | 33 | 33 | 33 | 100.00% | 100.00% | 100.00% |
| Total | 70 | 45 | 54 | 54 | | | |

In Group I (0-7 days post infection), about 56.25% of patients were negative for both IgM and IgG, 31.25% of patients developed IgM but not IgG, and 12.5% of patients developed IgM and IgG, clearly showing the presence of IgM preceding IgG as the initial immune response against COVID-19 infection. In Group II, 47.62% of patients developed both IgM and IgG compared to 19.05% of patients who were positive for IgM and negative for IgG within the same onset group. By >14 days post infection, 100% patients developed both IgG and IgM against SARS-CoV-2 (see FIG. 2(a)). Combined, the antibody positive rate for >6 days, >10 days and >14 (15-45) days were 75% for IgG and 86.67% for IgM, 87.76% for IgG and 93.87% for IgM, and 100% for IgG and 100% for IgM, respectively (see Table 4).

TABLE 4 shows positive agreement of pGOLD SARS-CoV-2 IgG/IgM assay against the S1 antigen according to days since PCR-positive COVID-19 serum samples were collected post symptom onset in the range of 6-45 days.

| Days from Symptom onset | Number of PCR+ samples | pGOLD sensitivity assay for IgG+ | pGOLD sensitivity assay for IgM+ | pGOLD sensitivity assay for IgG+ of IgM+ or both |
|---|---|---|---|---|
| ≥6 days | 60 | 45/60 = 75% (95% CI 62.77%-84.22%) | 51/60 = 86.67% (95% CI 75.83%-93.09%) | 51/60 = 86.67% (95% CI 75.83%-93.09%) |
| ≥10 days | 49 | 42/49 = 87.76% (95% CI 75.76%-94.27%) | 46/49 = 93.87% (95% CI 83.48%-97.89%) | 46/49 = 93.87% (95% CI 83.48%-97.89%) |
| ≥14 days | 33 | 33/33 = 100% (95% CI 89.5%-100%) | 33/33 = 100% (95% CI 89.5%-100%) | 33/33 = 100% (95% CI 89.5%-100%) |

The pGOLD™ SARS-CoV-2 antibody assay revealed a classical serological immune response behavior wherein IgM appears before IgG in the in the 0-14 days post infection acute phase. This differed from a recent serological-response study by ELISA that found the IgM positive rate below IgG at all times (see e.g., Long, Q.-X., et al. Nature Medicine (2020) 26(6):845-848). It has been suggested that low positive rate of IgM by ELISA could be due to insufficient analytical sensitivity, causing delays in the detection of IgM levels above background noise in PCR-confirmed COVID-19 patient samples. However, the high signal to background ratio of the present assay permits earlier detection of IgM antibodies. The pGOLD™ assay has near 100% sensitivity (for COVID-19 patient sera collected >14 days post infection) and 99.78% specificity in detecting both IgG and IgM subtypes (based on ~550 presumptive negative and positive samples, FIGS. 1(e), 2(b), and 2(c)).

Simultaneous Detection of Multiple Antibody Isotypes

In addition to increased analytical sensitivity, the pGOLD™ assay was capable of testing IgM and IgG antibodies in the same patient sample against multiple SARS-CoV-2 antigens simultaneously (see FIG. 1(a)), a unique feature among existing COVID-19 assays.

To investigate antibody responses to specific regions of the SARS-CoV-2 spike protein, antibodies against receptor binding domain (RBD) in the S1 subunit were measured and analyzed. Obtained was a maximum specificity of 99.78% for IgG (1/454 false positive, the same anti-S1 IgG false positive) and 99.78% for IgM (1/454 false positive, a different sample from the anti-S1 IgM false positive), and sensitivity of 100% for both IgG and IgM in PCR-confirmed COVID-19 patient samples at >14 days post disease symptom onset, suggesting that the pGOLD™ assay of antibodies against RBD was also both highly specific and sensitive (see Tables 5 and 6).

TABLE 5

Summary of pGOLD SARS-CoV-2 IgG/IgM assay results against the RBD antigen for 70 samples collected from PCR-positive COVID-19 patients at 0 to 7 (Group I), 8 to 14 (Group II), and 15 to 45 (Group III) days since symptom onset.

| Days since symptom onset | Number of samples | # IgG Positive | # IgM Positive | # Antibody Positive | % IgG Positive | % IgM Positive | % Antibody Positive |
|---|---|---|---|---|---|---|---|
| 0 to 7 | 16 | 3 | 6 | 6 | 18.75% | 37.50% | 37.50% |
| 8 to 14 | 21 | 9 | 14 | 14 | 42.86% | 66.67% | 66.67% |
| 15 to 45 | 33 | 33 | 33 | 33 | 100.00% | 100.00% | 100.00% |
| Total | 70 | 45 | 53 | 53 | | | |

TABLE 6

Shows the positive agreement of pGOLD SARS-CoV-2 IgG/IgM assay against the RBD antigen according to days since PCR-positive COVID-19 serum samples were collected post symptom onset in the range of 6-45 days.

| Days from Symptom onset | Number of PCR+ samples | pGOLD sensitivity assay for IgG+ | pGOLD sensitivity assay for IgM+ | pGOLD sensitivity assay for IgG+ of IgM+ or both |
|---|---|---|---|---|
| ≥6 days | 60 | 44/60 = 73.33% (95% CI 57.64%-79.76%) | 51/60 = 85% (95% CI 73.89%-91.90%) | 51/60 = 85% (95% CI 73.89-91.90%) |

TABLE 6-continued

Shows the positive agreement of pGOLD SARS-CoV-2 IgG/IgM assay against the RBD antigen according to days since PCR-positive COVID-19 serum samples were collected post symptom onset in the range of 6-45 days.

| Days from Symptom onset | Number of PCR+ samples | pGOLD sensitivity assay for IgG+ | pGOLD sensitivity assay for IgM+ | pGOLD sensitivity assay for IgG+ of IgM+ or both |
|---|---|---|---|---|
| ≥10 days | 49 | 42/49 = 85.71% (95% CI 73.33%-92.90%) | 46/49 = 93.87% (95% CI 83.48%-97.89%) | 46/49 = 93.87% (95% CI 83.48%-97.89%) |
| ≥14 days | 33 | 33/33 = 100% (95% CI 89.5%-100%) | 33/33 = 100% (95% CI 89.5%-100%) | 33/33 = 100% (95% CI 89.5%-100%) |

Figure 3:
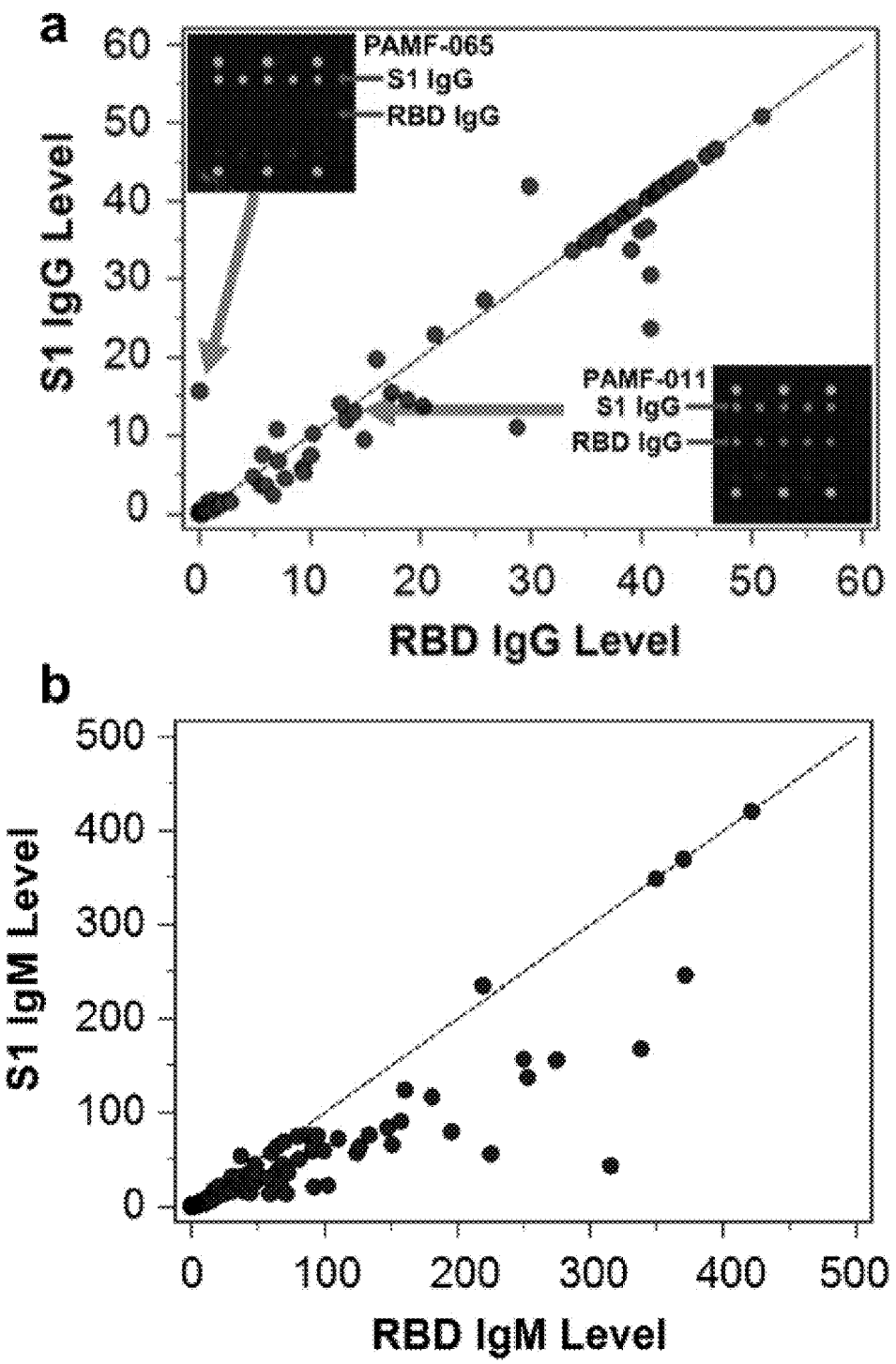
FIG. 3 (a) is a correlation plot of anti-S1 IgG level (y-axis) and anti-RBD IgG level (x-axis) measured in PCR-confirmed COVID-19 patient sera. The dashed line was drawn to have a slope of 1. The upper left inset shows the scanned image of the IgG-only channel in a patient serum labeled as PAMF-065, which displayed high signal on the S1 antigen but not on the RBD antigen. The lower right inset shows the scanned image of IgG levels of a sample labeled as PAMF-011, displaying about equal IgG signals against S1 and RBD. (b) is a correlation plot of anti-S1 IgM level (y-axis) and anti-RBD IgM level (x-axis) measured in COVID-19 patient sera. The dashed line was drawn to have a slope of 1.

Correlation analysis of antibodies in COVID-19 sera against S1 and RBD deviated from linear relations, with IgG levels against the two antigens scattered around the slope=1 line (see FIG. 3(a)). The IgM levels against S1 and RBD were scattered with a fit-line slope well below 1, suggesting substantially higher IgM binding to RBD than to S1 (see FIG. 3(b)).

The RBD in the S1 subunit in the SARS-CoV-2 spike protein was responsible for binding to the ACE2 receptor on host cells to initiate infection, and was generally recognized as an important target for both neutralization antibody treatment and specific SARS-CoV-2 detection. These results showed that the S1 and RBD antigens were both highly specific and sensitive SARS-CoV-2 antibody targets, while complementing each other in sensitivity to a discernable degree (see Table 7). To exploit the two-plex capability, it was possible to combine antibodies against S1 and RBD to increase the pGOLD™ assay sensitivity for the <14-day sample group for IgG and IgM, from 32.43% against S1 only to 37.84% combined and 54.05% against RBD only to 56.76% combined, respectively.

TABLE 7

Shows comparisons of pGOLD SARS-CoV-2 IgG/IgM assay results of PCR-positive patient samples (with known data on days since symptom onset) against the S1 and RBD antigens. The IgG positive status of a sample was determined if the IgG level was >1.79 and >1.62 for RBD and S1, respectively. The IgM positive status of a sample was determined if the IgM level was >3 and >1.38 for RBD and S1, respectively.

| Sample source | Sample ID | RT-PCR Result | Days since symptom onset | RBD IgM Level | RBD IgG Level | S1 IgM Level | S1 IgG Level | RBD IgM Status | RBD IgG Status | S1 IgM Status | S1 IgG Status |
|---|---|---|---|---|---|---|---|---|---|---|---|
| PAMF | 8 | Positive | 0 | -0.38 | 0.00 | -0.57 | 0.05 | neg | neg | neg | neg |
| PAMF | 5 | Positive | 1 | -0.40 | 0.00 | -0.51 | 0.02 | neg | neg | neg | neg |
| PAMF | 20 | Positive | 1 | 0.02 | 0.00 | -0.18 | 0.06 | neg | neg | neg | neg |
| CDPH | 8 | Positive | 2 | 0.69 | 0.00 | 0.26 | 0.02 | neg | neg | neg | neg |
| PAMF | 12 | Positive | 2 | 8.70 | 1.01 | 4.65 | 0.62 | pos | neg | pos | neg |
| PAMF | 17 | Positive | 3 | 11.86 | 2.08 | 7.86 | 1.50 | pos | pos | pos | neg |
| PAMF | 4 | Positive | 4 | -0.04 | 0.06 | 0.03 | 0.05 | neg | neg | neg | neg |
| PAMF | 21 | Positive | 4 | 0.33 | 0.22 | 0.12 | 0.11 | neg | neg | neg | neg |
| PAMF | 6 | Positive | 5 | -0.33 | 0.00 | -0.32 | 0.01 | neg | neg | neg | neg |
| PAMF | 7 | Positive | 5 | -0.42 | 0.02 | -0.53 | 0.07 | neg | neg | neg | neg |
| CDPH | 2.34 | Positive | 6 | 4.77 | 0.27 | 2.60 | 0.14 | pos | neg | pos | neg |
| PAMF | 65 | Positive | 6 | -0.37 | 0.03 | 2.00 | 15.67 | neg | neg | pos | pos |
| CDPH | 2.37 | Positive | 7 | 72.16 | 28.76 | 36.23 | 11.11 | pos | pos | pos | pos |
| PAMF | 15 | Positive | 7 | 9.67 | 1.81 | 7.01 | 1.07 | pos | pos | pos | neg |
| PAMF | 74 | Positive | 7 | 5.08 | 1.53 | 3.30 | 1.00 | pos | neg | pos | neg |
| PAMF | 100 | Positive | 7 | 0.52 | 0.02 | 0.54 | 0.01 | neg | neg | neg | neg |
| CDPH | 16 | Positive | 8 | 0.26 | 0.08 | 0.92 | 0.04 | neg | neg | neg | neg |
| PAMF | 64 | Positive | 8 | 0.02 | 0.07 | -0.45 | 0.06 | neg | neg | neg | neg |
| PAMF | 102 | Positive | 8 | 4.22 | 1.57 | 2.00 | 0.99 | pos | neg | pos | neg |
| CDPH | 6 | Positive | 9 | 1.34 | 0.50 | 1.37 | 0.37 | neg | neg | neg | neg |
| PAMF | 70 | Positive | 9 | 1.41 | 0.10 | 0.56 | 0.03 | neg | neg | neg | neg |
| CDPH | 2 | Positive | 10 | 29.28 | 7.15 | 24.52 | 6.74 | pos | pos | pos | pos |
| CDPH | 2.1 | Positive | 10 | 8.92 | 0.35 | 6.26 | 0.24 | pos | neg | pos | neg |
| PAMF | 78 | Positive | 10 | 1.17 | 0.12 | 1.24 | 0.18 | neg | neg | neg | neg |
| CDPH | 2.32 | Positive | 11 | 14.56 | 6.02 | 6.97 | 3.64 | pos | pos | pos | pos |
| CDPH | 2.18 | Positive | 12 | 421.35 | 41.51 | 421.35 | 41.50 | pos | pos | pos | pos |
| CDPH | 2.28 | Positive | 12 | 30.08 | 20.28 | 15.92 | 13.67 | pos | pos | pos | pos |
| CDPH | 2.29 | Positive | 12 | 44.93 | 39.90 | 25.35 | 36.20 | pos | pos | pos | pos |
| PAMF | 14 | Positive | 12 | 3.58 | 1.08 | 2.75 | 1.44 | pos | neg | pos | pos |
| PAMF | 73 | Positive | 12 | 3.34 | 0.78 | 2.77 | 1.37 | pos | neg | pos | neg |
| CDPH | 2.4 | Positive | 13 | 6.86 | 1.22 | 3.10 | 1.67 | pos | neg | pos | pos |
| CDPH | 5 | Positive | 13 | 16.53 | 7.03 | 17.72 | 10.82 | pos | pos | pos | pos |
| PAMF | 101 | Positive | 13 | 6.61 | 10.27 | 5.15 | 10.33 | pos | pos | pos | pos |
| PAMF | 115 | Positive | 13 | -0.08 | 0.01 | -0.02 | -0.03 | neg | neg | neg | neg |

TABLE 7-continued

Shows comparisons of pGOLD SARS-CoV-2 IgG/IgM assay results of PCR-positive
patient samples (with known data on days since symptom onset) against the S1 and RBD
antigens. The IgG positive status of a sample was determined if the IgG level was >1.79 and
>1.62 for RBD and S1, respectively. The IgM positive status of a sample was determined if the
IgM level was >3 and >1.38 for RBD and 51, respectively.

| Sample source | Sample ID | RT-PCR Result | Days since symptom onset | RBD IgM Level | RBD IgG Level | S1 IgM Level | S1 IgG Level | RBD IgM Status | RBD IgG Status | S1 IgM Status | S1 IgG Status |
|---|---|---|---|---|---|---|---|---|---|---|---|
| CDPH | 14 | Positive | 14 | 369.91 | 37.07 | 369.74 | 37.03 | pos | pos | pos | pos |
| CDPH | 15 | Positive | 14 | 17.41 | 16.06 | 15.74 | 19.76 | pos | pos | pos | pos |
| PAMF | 114 | Positive | 14 | 1.07 | 0.14 | 1.13 | 0.21 | neg | neg | neg | neg |
| CDPH | 2.6 | Positive | 15 | 94.42 | 39.11 | 75.64 | 33.75 | pos | pos | pos | pos |
| CDPH | 7 | Positive | 15 | 63.92 | 37.08 | 64.09 | 37.01 | pos | pos | pos | pos |
| CDPH | 9 | Positive | 15 | 349.33 | 35.09 | 349.14 | 35.01 | pos | pos | pos | pos |
| CDPH | 2.8 | Positive | 16 | 88.08 | 41.25 | 75.82 | 41.21 | pos | pos | pos | pos |
| CDPH | 2.21 | Positive | 17 | 274.49 | 43.33 | 156.57 | 43.24 | pos | pos | pos | pos |
| CDPH | 2.22 | Positive | 17 | 252.71 | 41.68 | 137.63 | 41.63 | pos | pos | pos | pos |
| CDPH | 2.27 | Positive | 17 | 48.47 | 36.60 | 26.60 | 36.56 | pos | pos | pos | pos |
| CDPH | 2.31 | Positive | 18 | 48.64 | 45.90 | 35.45 | 45.85 | pos | pos | pos | pos |
| CDPH | 2.36 | Positive | 18 | 249.57 | 46.82 | 157.49 | 46.70 | pos | pos | pos | pos |
| PAMF | 13 | Positive | 18 | 16.84 | 21.36 | 17.48 | 22.86 | pos | pos | pos | pos |
| CDPH | 2.26 | Positive | 19 | 99.78 | 36.23 | 59.71 | 36.18 | pos | pos | pos | pos |
| PAMF | 10 | Positive | 19 | 36.68 | 39.18 | 31.64 | 39.12 | pos | pos | pos | pos |
| PAMF | 16 | Positive | 19 | 48.35 | 34.91 | 43.81 | 34.81 | pos | pos | pos | pos |
| CDPH | 2.13 | Positive | 20 | 219.25 | 37.47 | 235.55 | 37.42 | pos | pos | pos | pos |
| CDPH | 2.24 | Positive | 20 | 147.42 | 38.29 | 84.09 | 38.25 | pos | pos | pos | pos |
| CDPH | 2.3 | Positive | 20 | 126.42 | 41.16 | 63.92 | 41.09 | pos | pos | pos | pos |
| CDPH | 2.25 | Positive | 21 | 124.12 | 33.79 | 57.16 | 33.72 | pos | pos | pos | pos |
| CDPH | 2.2 | Positive | 22 | 69.31 | 36.77 | 68.65 | 36.69 | pos | pos | pos | pos |
| CDPH | 2.35 | Positive | 22 | 37.40 | 43.17 | 53.51 | 43.11 | pos | pos | pos | pos |
| CDPH | 2.19 | Positive | 23 | 91.08 | 37.18 | 68.09 | 37.11 | pos | pos | pos | pos |
| PAMF | 9 | Positive | 23 | 80.63 | 41.34 | 50.69 | 41.26 | pos | pos | pos | pos |
| PAMF | 11 | Positive | 23 | 10.13 | 14.00 | 5.20 | 13.01 | pos | pos | pos | pos |
| PAMF | 22 | Positive | 23 | 13.28 | 13.26 | 6.38 | 12.05 | pos | pos | pos | pos |
| CDPH | 2.38 | Positive | 25 | 69.01 | 42.79 | 44.57 | 42.68 | pos | pos | pos | pos |
| CDPH | 2.12 | Positive | 26 | 224.75 | 36.07 | 55.89 | 35.21 | pos | pos | pos | pos |
| CDPH | 2.7 | Positive | 26 | 59.84 | 38.48 | 56.78 | 38.43 | pos | pos | pos | pos |
| CDPH | 2.14 | Positive | 27 | 20.75 | 39.08 | 21.91 | 39.01 | pos | pos | pos | pos |
| CDPH | 2.16 | Positive | 27 | 195.37 | 40.50 | 79.72 | 40.39 | pos | pos | pos | pos |
| CDPH | 2.17 | Positive | 27 | 133.82 | 37.44 | 76.70 | 37.36 | pos | pos | pos | pos |
| CDPH | 2.11 | Positive | 32 | 47.91 | 41.14 | 44.62 | 41.09 | pos | pos | pos | pos |
| CDPH | 2.15 | Positive | 36 | 42.79 | 38.77 | 34.18 | 38.72 | pos | pos | pos | pos |
| PAMF | 18 | Positive | 38 | 157.27 | 36.24 | 90.97 | 36.20 | pos | pos | pos | pos |
| CDPH | 2.9 | Positive | 45 | 29.91 | 42.48 | 31.74 | 42.43 | pos | pos | pos | pos |

FIG. 3(a) shows an extreme case of a COVID-19 patient serum (labeled PAMF-065) that showed SARS-CoV-2 IgG only binding to S1 and not to RBD. A recent study identified distinct groups of phage-display derived antibodies against SARS-CoV-2 that bind preferentially to RBD or S140. Our results could reflect a similar phenomenon in COVID-19 human serum. Additional research may be conducted concerning immune responses to SARS-CoV-2 and the antibody-antigen interactions at the molecular level to show this.

Development of a pGOLD™ Avidity Test

A pGOLD™ SARS-CoV-2 IgG avidity test was developed to further investigate antibody-antigen binding affinity and stability in denaturing conditions. Antibodies developed shortly after a primary infection exhibit low avidity and bind weakly to the antigen. Over time, avidity towards antigens can increase as antibodies 'mature' through colonial expansion, hypermutation and affinity selection in the germinal center. Accordingly, antibody avidity measurements may provide further information about the time since infection. This could be particularly important if COVID-19 returns in subsequent waves and in upcoming influenza seasons. The SARS-CoV-2 IgG avidity test herein included a denaturing 6 M urea-treatment step to remove weakly bound antibodies on the antigen, leaving only the antibodies with a strong affinity for the antigens to be detected.

It was discovered that IgG against S1 and RBD in all COVID-19 patient sera except for one (PAMF-065). PAMF-065 showed low avidity between 0 and 0.3 (see FIG. 4(a) and Table 8). This suggested recent infections because all of the IgG-positive COVID-19 samples (49/70 PCR-positive tested for avidity) were collected within 6-45 days post infection. A slight trend of higher anti-S1 IgG avidity vs. the number of days of post symptom onset was discerned (see FIG. 4(a)). Also noticeable was a lower average anti-RBD IgG avidity than anti-S1 IgG avidity (see FIG. 4(a)).

TABLE 8

Shows pGOLD SARS-CoV-2 IgG avidity assay results of IgG-positive, PCR-confirmed COVID-19 patient samples (in the range of 6-45 days post symptom onset) against the S1 and RBD antigens. The samples were treated with and without 6M urea and an avidity index was calculated by dividing the IgG signals of the urea-treated samples by the IgG signals of the non-treated sample for the respective antigen.

| Sample source | Sample ID | Days since symptom onset | S1 Untreated IgG MFI | S1 6M Urea-treated IgG MFI | S1 Avidity Index | RBD Untreated IgG MFI | RBD 6M Urea-treated IgG MFI | RBD Avidity Index |
|---|---|---|---|---|---|---|---|---|
| PAMF | 65 | 6 | 10456.17 | 8872.33 | 0.85 | NA | NA | NA |
| CDPH | 2.37 | 7 | 707.17 | 10.00 | 0.01 | 2214.50 | 4.33 | 0.00 |
| PAMF | 15 | 7 | 512.83 | 14.00 | 0.03 | 743.00 | 4.67 | 0.01 |
| PAMF | 102 | 8 | 515.50 | 17.00 | 0.03 | 514.17 | 8.33 | 0.02 |
| CDPH | 2 | 10 | 1675.17 | 19.33 | 0.01 | 1182.33 | −36.83 | −0.03 |
| CDPH | 2.32 | 11 | 870.67 | 14.33 | 0.02 | 1220.83 | 12.33 | 0.01 |
| CDPH | 2.29 | 12 | 19303.50 | 379.33 | 0.02 | 216.83 | 4.67 | 0.02 |
| PAMF | 14 | 12 | 324.67 | 17.33 | 0.05 | 5987.00 | 3.67 | 0.00 |
| CDPH | 2.28 | 12 | 5193.83 | 25.67 | 0.00 | 217.50 | 1.17 | 0.01 |
| PAMF | 73 | 12 | 410.67 | 18.00 | 0.04 | 19612.17 | 94.33 | 0.00 |
| CDPH | 2.18 | 12 | 45554.00 | 7471.50 | 0.16 | 39149.17 | 204.33 | 0.01 |
| CDPH | 5 | 13 | 3136.00 | 26.67 | 0.01 | 319.33 | 2.00 | 0.01 |
| CDPH | 2.4 | 13 | 621.67 | 10.67 | 0.02 | 2091.17 | 4.33 | 0.00 |
| PAMF | 101 | 13 | 4829.17 | 118.67 | 0.02 | 2550.00 | 27.33 | 0.01 |
| CDPH | 15 | 14 | 5017.83 | 319.00 | 0.06 | 24448.50 | 33.00 | 0.00 |
| CDPH | 14 | 14 | 36119.83 | 3098.67 | 0.09 | 3833.33 | 6.00 | 0.00 |
| CDPH | 7 | 15 | 35329.17 | 1376.00 | 0.04 | 37507.17 | 104.00 | 0.00 |
| CDPH | 2.6 | 15 | 7136.83 | 153.83 | 0.02 | 33893.83 | 32.00 | 0.00 |
| CDPH | 9 | 15 | 44496.00 | 3858.33 | 0.09 | 5862.67 | −30.33 | −0.01 |
| CDPH | 2.8 | 16 | 53572.17 | 3365.17 | 0.06 | 54150.33 | 99.00 | 0.00 |
| CDPH | 2.21 | 17 | 35587.83 | 10853.83 | 0.30 | 16938.50 | 263.83 | 0.02 |
| CDPH | 2.22 | 17 | 65442.33 | 6419.17 | 0.10 | 57113.17 | 299.67 | 0.01 |
| CDPH | 2.27 | 17 | 65431.67 | 2070.67 | 0.03 | 65437.33 | 98.33 | 0.00 |
| PAMF | 13 | 18 | 4680.00 | 318.50 | 0.07 | 65450.00 | 3662.83 | 0.06 |
| CDPH | 2.31 | 18 | 65446.67 | 4374.00 | 0.07 | 58531.67 | 6077.33 | 0.10 |
| CDPH | 2.36 | 18 | 60468.00 | 5845.17 | 0.10 | 4650.33 | 221.00 | 0.05 |
| PAMF | 16 | 19 | 64600.33 | 4361.33 | 0.07 | 47921.00 | 4972.33 | 0.10 |
| CDPH | 2.26 | 19 | 44727.00 | 1193.67 | 0.03 | 40300.50 | 4376.00 | 0.11 |
| PAMF | 10 | 19 | 46299.17 | 4255.83 | 0.09 | 34217.67 | 100.00 | 0.00 |
| CDPH | 2.3 | 20 | 50803.83 | 2773.50 | 0.05 | 36666.50 | 4893.83 | 0.13 |
| CDPH | 2.13 | 20 | 65437.67 | 6894.00 | 0.11 | 38427.50 | 193.17 | 0.01 |
| CDPH | 2.24 | 20 | 51132.00 | 1832.17 | 0.04 | 55682.67 | 261.33 | 0.00 |
| CDPH | 2.25 | 21 | 65433.33 | 5994.83 | 0.09 | 58754.00 | 297.00 | 0.01 |
| CDPH | 2.35 | 22 | 65431.67 | 9695.33 | 0.15 | 65438.00 | 10464.17 | 0.16 |
| CDPH | 2.2 | 22 | 65335.00 | 4239.33 | 0.06 | 64295.83 | 232.33 | 0.00 |
| PAMF | 11 | 23 | 2868.00 | 418.67 | 0.15 | 46869.33 | 3470.67 | 0.07 |
| CDPH | 2.9 | 45 | 59050.33 | 12739.33 | 0.22 | 38435.17 | 405.83 | 0.01 |

In addition to assessing recent/remote infection and primary/secondary infection, multiplexed measurements of avidity towards a panel of antigens is useful for understanding many aspects of an immune response. For example, avidity measurements are useful for understanding the immune response to SARS-CoV-2 and how antibodies mature, with implications for immunity and convalescent plasma based antibody therapy. Avidity is also useful for assessing vaccine efficacy and can help guide vaccine development. A better vaccine would elicit higher Ab levels and the Abs will have higher avidity.

Figure 4:
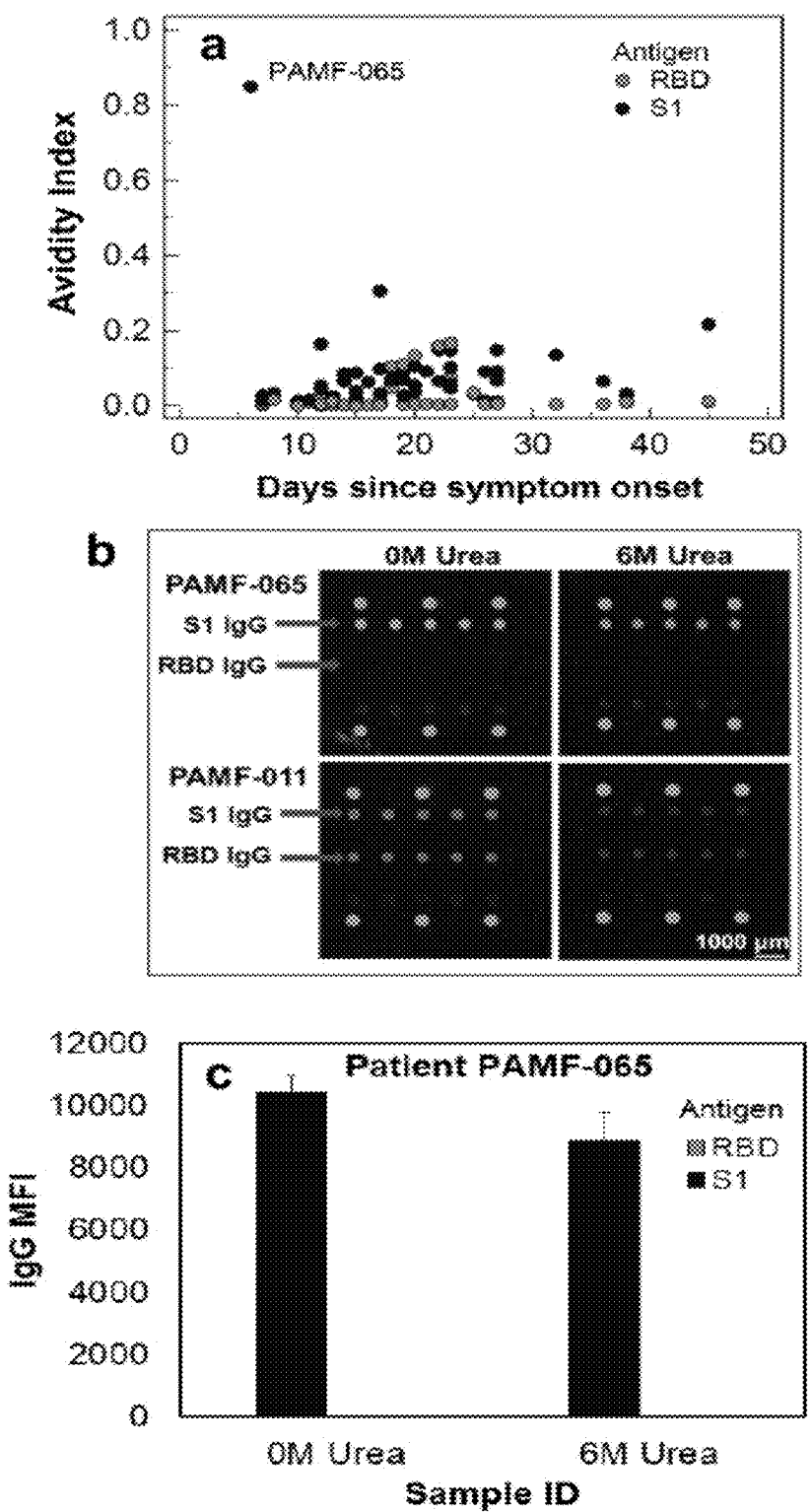
FIG. 4 (a) illustrates avidity of anti-S1 IgG and anti-RBD IgG measured in IgG-positive, PCR-confirmed COVID-19 patient sera collected 6-45 days post symptom onset. The serum of PAMF-065 showed unusually high avidity for anti-S1 IgG while being negative for anti-RBD IgG. (b) are fluorescence images with the upper panel showing fluorescence images of IgG-only channel showing PAMF-065 serum sample with high anti-S1 IgG level with and without urea treatment, hence high avidity. It showed negligible anti-RBD IgG. The lower panel shows fluorescence images of another patient serum tested, PAMF-011, with much reduced anti-S1 IgG level after urea treatment, indicating low avidity. Low avidity was observed for all samples except PAMF-065. (c) illustrates anti-S1 IgG median fluorescence intensity (MFI) signals of the PAMF-065 sample with and without urea treatment. The error bars indicate one standard deviation away from the mean.

Unexpectantly, the sample PAMF-065 (with antibody binding only to S1 and not to RBD in see FIGS. 3(a) and 4(b)) collected from a PCR-confirmed COVID-19 patient showed a strong anomaly in anti-S1 IgG avidity with a high value of ~0.8, typically interpreted as infection >6 months ago. Also interesting was that the serum sample used for pGOLD™ antibody assay was collected from the patient only ~6 days post COVID-19 symptom onset, yet showed a high anti-S1 IgG level at ~10 times of cutoff with only a low positive IgM against S1. The patient was a 73 years old woman tested SARS-CoV-2 positive by PCR at 6 days (same day as serum sample was obtained) post the onset of symptoms (fever, lymphopenia). Prior to the diagnosis she had likely been exposed to SARS-CoV-2 for several weeks from her mother who died of COVID-19. She did not develop pneumonia and did not get much sicker despite her relatively advanced age, suggesting a degree of immunity. Accordingly the PAMF-65 patient was diagnosed as having re-infection based on the high IgG against SARS-CoV-2 S1 at 6 days post symptom onset, low positive IgM, and unusually high IgG avidity. It was possible that the patient was previously exposed to a closely related infection including SARS-CoV-1 with antibodies cross-react with SARS-CoV-2. This result was intriguing and underscored the usefulness and importance of antibody avidity testing for COVID-19.

Sensitivity of pGold Assay in Saliva Samples

The high analytical sensitivity of the nano-gold plasmonic platform was used for detecting antibodies in human saliva against SARS-CoV-2. It is well known that antibody concentration in human saliva is orders of magnitude lower than in blood or serum, demanding assay platforms with exquisite analytical sensitivity and capable of detecting ultra-high signal over background noise (see e.g., Li, X., et al. (2019) Plasmonic gold chips for the diagnosis of *Toxoplasma gondii*, CMV, and rubella infections using saliva with serum detection precision. European journal of clinical microbiology & infectious diseases: official publication of the European Society of Clinical Microbiology 38, 883-890).

Figure 5:
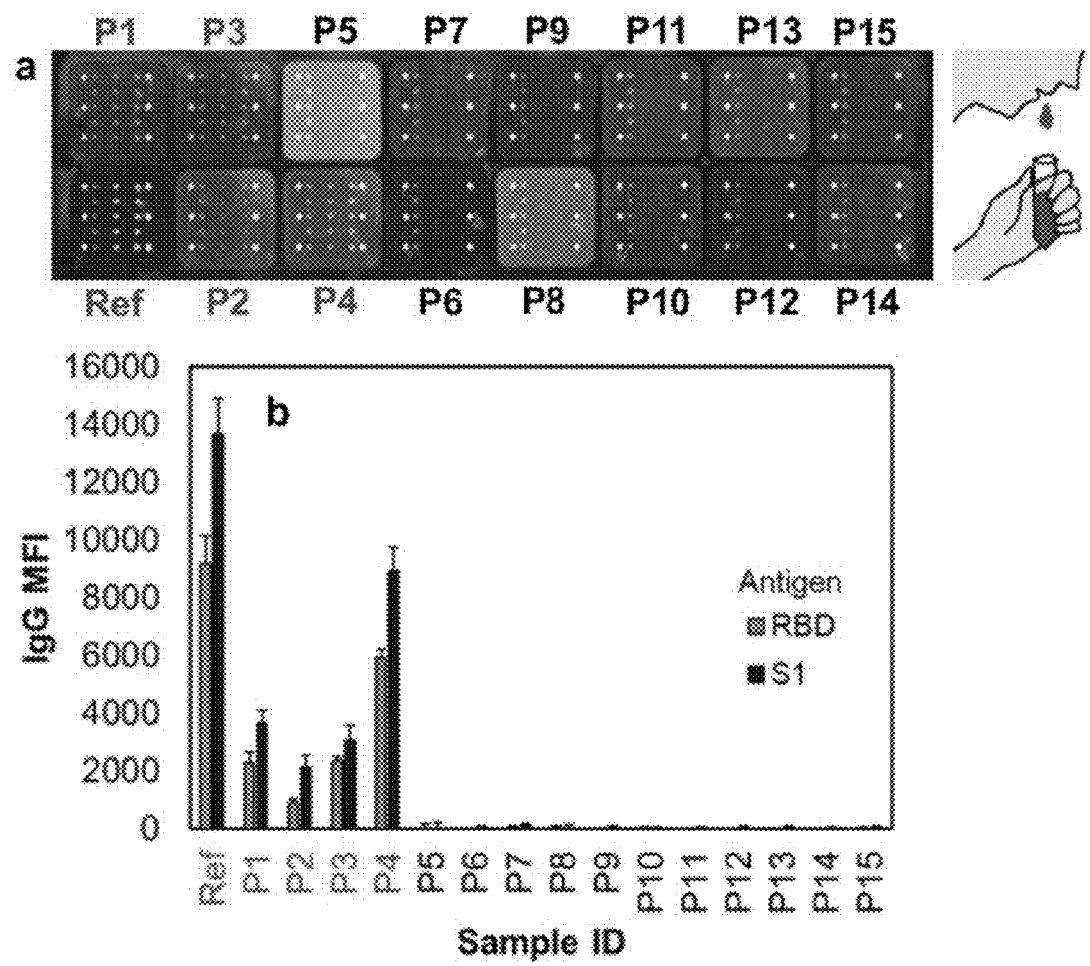
FIG. 5 (a) is a confocal fluorescence image of IgG signals in the saliva of 4 recovered COVID-19 patients (denoted as P1-P4) and 11 healthy controls (denoted as P5-P15) and a 104 times diluted serum of a PCR-confirmed COVID-19 patient as a reference (denoted as 'Ref'). Saliva was collected by a simple spitting method as shown in the schematic. (b) illustrate median fluorescence intensity (MFI) signals of anti-S1 and anti-RBD IgG measured in the saliva samples and PCR-positive COVID-19 serum reference with background signals subtracted. The error bars indicate one standard deviation away from the mean.

Saliva samples of 4 fully recovered, PCR-positive COVID-19 patients and 11 healthy individuals on the pGOLD™ SARS-CoV-2 antibody assay (see FIG. 5(a)) were tested. Although background fluorescence signals were observed for some saliva samples, likely due to autofluorescence of molecules in the saliva, background-subtracted IgG signals on S1 and RBD antigens allowed clear differentiation of positive COVID-19 recovered patient saliva from healthy controls (see FIG. 5(b)). This promising result suggested the first multiplexed saliva-based antibody test for SARS-CoV-2, which could greatly facilitate population-based mass screening of COVID-19. Note that a COVID-19 patient serum diluted by 104 times was included in the assay (labeled 'REF' in FIG. 5(b)) and showed similar IgG level as in the COVID-19 positive saliva samples.

With about 100% sensitivity two weeks post infection and about 99.78% specificity based on >450 negative samples, the pGOLD™ COVID-19 IgG/IgM assay can be used for population-based mass screening, and sero-surveillance and prevalence studies. The clear trend of IgM detection prior to IgG could be used to aid COVID-19 diagnosis starting from the early stage. A highly sensitive and specific IgM test could facilitate diagnosis of re-infection or secondary infection in the acute phase in a future return of SARS-CoV-2. An important finding was that multiplexed IgG avidity measurements against multiple virial antigens could facilitate understanding of the immune responses and antibody maturation, and aid the differentiation of primary from secondary infection, and reveal the infection timing. A technically unique feature is the high capability of antibody detection in human saliva samples on the novel nanotechnology based pGOLD™ platform which permits non-invasive home sample collection for mass-screening.

Biological Samples and Materials

74 PCR-confirmed COVID-19 patient serum samples were provided by the California Department of Public Health (CDPH) and the Dr. Jack S. Remington Laboratory for Specialty Diagnostics (JSRLSD) at the Palo Alto Medical Foundation. These samples were provided with information on the number of days between sample collection and disease symptom onset, excluding for 4. Another set of PCR-confirmed COVID-19 sera (with no known information on the number of days between disease onset to sample collection) were obtained from Baptist Health South Florida and Loma Linda Medical Center. 33 PCR-negative samples were provided by CDPH and Loma Linda Medical Center. 311 pre-pandemic serum samples collected in 2017-2019 were from the JSRLSD lab. 40 healthy control samples were acquired from the Arizona State University Health Services for projects before the SARS-CoV-2 outbreak. 70 samples from patients with various diseases for cross-reactivity checking were provided by Loma Linda Medical Center, CDPH, Valley Medical Center in San Jose, the JSRLSD lab, or purchased commercially. Saliva samples were collected through a simple spitting method into a plastic tube (see FIG. 5(a)) from healthy donors and fully recovered COVID-19 patients who tested positive by PCR over a month before collection. Saliva was diluted two times and centrifuged to remove any aggregates, and the supernatant was tested on the pGOLD™ assay.

IRDye800 CW NHS ester (LI-COR Biosciences) and CF-647 NHS ester (Millipore Sigma, SCJ4600048) were conjugated to anti-human IgG and anti-human IgM, respectively. The IRDye800-labeled anti-human IgG and CF-647-labeled anti-human IgM were used for two-color simultaneous detection of IgG and IgM against S1 and RBD antigens on pGOLD™.

Multiplexed SARS-CoV-2 Microarray Printing on pGOLD™ Slides

Each pGOLD™ slide (Nirmidas Biotech Inc.) was printed with two SARS-CoV-2 antigens, namely the spike protein S1 subunit (S1) and S1 containing the receptor binding domain (RBD), using a GeSiM Nano-Plotter 2.1 at the following concentrations: 60 µg/mL for S1 (40591-V08H, Sino Biological Inc.) and 25 µg/mL for RBD (40592-V08H, Sino Biological Inc.). On the same biochip, 7.5 µg/mL human IgG and 50 µg/mL BSA-biotin (Thermo Fisher Scientific) were also printed to serve as a printing control and "intra-well signal normalizer", respectively. The antigens were printed in quintuplicate for capturing SARS-CoV-2 antibodies in either serum, plasma, whole blood, or saliva (the current work focused on serum and saliva). Identical microarrays were printed on 16 isolated wells in each pGOLD™ biochip with a total of 4 biochips resembling a 64-well plate using the FAST frame incubation chamber (Millipore Sigma). The SARS-CoV-2 antigen-printed biochips were vacuum sealed and stored at −80° C. until use.

Multiplexed pGOLD™ SARS-CoV-2 IgG/IgM Assay Procedure

Serum samples were heated at 56° C. for 30 minutes to deactivate and reduce potential risk from any residual virus. The heat-deactivated serum samples were immediately used or stored at −80° C. for later use. The pGOLD™ antibody assays were performed in a 16-well format in the following steps: 1) Blocking: All wells were blocked with a blocking buffer for 30 minutes at room temperature, 2) Sample incubation: each well was then incubated with 100 µL of diluted patient serum (200× diluted in a dilution buffer) or saliva (2× dilution) for 60 minutes at room temperature. A positive control (diluted patient serum) and blank control (dilution buffer only) were also included in each biochip. 3) Secondary antibody incubation: each well was subsequently incubated with a mixture of 4 nM IRDye800-labeled anti-human IgG secondary antibody, 4 nM CF-647-labeled anti-human IgM secondary antibody, and 6 nM CF-647-labeled streptavidin for 30 minutes at room temperature (see FIG. 1(a)). Note that each well was washed three times with PBST (PBS with 0.05 Tween 20) between steps. The CF-647-labeled streptavidin in the detection step binds to BSA-biotin spots in each well on the pGOLD™ biochip, and the signal was used as an "intrawell signal normalizer". That is, the IgG and IgM signals were divided by the intrawell normalizing signal to obtain a ratio index for IgG and IgM of each sample. Intrawell normalization was designed to minimize the effect of slight differences in pGOLD™ film uniformity across each biochip which may affect fluorescence enhancement.

pGOLD™ SARS-CoV-2 IgG Avidity Assay

The pGOLD™ SARS-CoV-2 IgG avidity in a serum sample was measured by detecting captured IgG for the sample with and without urea treatment, side-by-side, in two neighboring pGOLD™ wells. In each well, 0.5 L of the same serum sample was diluted 200 times. In one well, a regular IgG assay was performed, whereas in the neighboring well the same IgG assay was performed except that a 10-minute treatment with 6 M urea was added following the sample incubation step. Such treatment by a denaturing agent like urea detaches the IgG from the antigen spot if the IgG avidity is low. At the end of the assay, the IgG signal of the urea-treated sample was divided by the IgG signal of the regularly assayed sample, giving an avidity index value.

Thus, dividing the IgG level measured on each antigen with denaturing agent by the IgG level measured in the absence of denaturing agent, wherein when the ratio is about 0.5 or less, the avidity is low and when the ratio is about 0.5 or greater, the avidity is high, and wherein IgG avidity for antibodies against antigens comprising at least one of a SARS-CoV-2 S1 subunit, an RBD, a S2 subunit or nucleocapsid protein, SARS-CoV-1 antigens, MERS antigens, and a common cold antigen comprising human coronaviruses 229E, NL63, OC43, and HKU1 is measured in a single assay.

Data Analysis

After the assay procedures, a dual-channel MidaScan™ microarray scanner (provided by Nirmidas Biotech, Inc.) was used to scan each biochip for IRDye800-conjugated anti-human IgG and CF-647-conjugated anti-human IgM signals on the SARS-CoV-2 antigen spots. CF-647 and IRDye800 fluorescence images in the respective red and green channels were generated and the median fluorescence signal (MFI) for each microarray was quantified by the MidaScan™ Software version 2.0.0. The data was used to calculate the average MFI with the antigen spots of the highest and lowest MFIs removed for each channel, thus lending to a single signal intensity used to measure antibody detection in each sample. Afterwards, the MFI was normalized to the average intrawell MFI signal, resulting in an intrawell ratio, and adjusted by a factor of 100 for IgM and 10 for IgG. The final values were used to determine antibody status of the samples for the corresponding antigen. Cutoffs were determined by ROC curve analysis using MedCalc Statistical Software version 19.2.1 (MedCalc Software Ltd., Ostend, Belgium). The method disclosed herein resulted in an effective combination of sensitivity and specificity of the multiplexed assay on pGOLD™.

Certain modifications and improvements will occur to those skilled in the art upon a reading of the foregoing description. It should be understood that all such modifications and improvements have been deleted herein for the sake of conciseness and readability but are properly within the scope of the following claims.

We claim:

1. A method for diagnosing or prognosticating SARS-CoV-2 infection, COVID-19, or a combination of SARS-CoV-2 infection and COVID-19, in a subject in need thereof, the method comprising:
   (a) obtaining, or having obtained, a saliva sample from the subject;
   (b) diluting the saliva sample two times in a buffer solution;
   (c) contacting the saliva sample to at least two SARS-CoV-2 antigens, wherein the at least two SARS-CoV-2 antigens are bound on a plasmonic substrate, and wherein the at least two SARS-CoV-2 antigens specifically binds to at least two IgM, IgG, or IgA antibody in the saliva sample to form immune complexes;
   (d) contacting the IgG, IgM, or IgA immune complexes with an organic dye labeled antihuman IgG, antihuman IgM and antihuman IgA antibodies, wherein the organic dye labeled antihuman IgG, antihuman IgM, and antihuman IgA antibodies are each labeled with a different organic dye that fluoresces at a non-overlapping emission wavelength,
   (e) detecting fluorescence intensities of the organic dyes to diagnose SARS-CoV-2 infection, COVID-19, or a combination of SARS-CoV-2 infection and COVID-19, wherein the fluorescence intensity is proportional to the amount of IgM, IgG, or IgA antibody in the sample, and wherein the proportion of IgM, IgG, or IgA antibody in the sample correlates with the time since SARS-CoV-2 infection, and
   (f) treating the subject diagnosed with SARS-CoV-2 infection, COVID-19, or a combination of SARS-CoV-2 infection and COVID-19, with a compound or other therapy to mitigate symptoms, prevent spread of SARS-CoV-2 infection, facilitate therapy for others, and/or improve symptoms of COVID-19, or a combination thereof.

2. The method of claim 1, wherein the plasmonic substrate is a plasmonic gold, silver, aluminum, copper, glass, quartz, plastic or nitrocellulose substrate.

3. The method of claim 2, wherein the substrate comprises a metallic film arranged discontinuously on the substrate wherein the metallic film has isolated island areas of between about 100 nm$^2$ and 250,000 nm$^2$ in surface-exposed area, the isolated islands being separated by gaps of about 10 nm to about 60 nm.

4. The method of claim 2, wherein the plasmonic substrate is a plasmonic gold substrate.

5. The method of claim 1, wherein the at least two SARS-CoV-2 antigens are coated on the substrate at distinct locations.

6. The method of claim 1, wherein the at least two SARS-CoV-2 antigens are selected from the group consisting of a SARS-CoV-2 S1 subunit, a receptor binding domain (RBD), an S2 subunit, a nucleocapsid protein, and combinations thereof.

7. The method of claim 6, wherein the at least two SARS-CoV-2 antigens are SARS-CoV-2 S1 and RBD.

8. The method of claim 1, wherein the at least two SARS-CoV-2 antigens are a SARS-CoV-2 antigen variant selected from the group consisting of variants:
   (i) N501Y;
   (ii) K417N, E484K, and N501Y;
   (iii) E484K; K417N;
   (iv) L452R and E484Q;
   (v) K417T, E484K, and N501Y;
   (vi) K417T;
   (vii) HV69-70 deletion, a Y144 deletion, N501Y, A570D, D614G, P681H, T716I, S982A, and D1118H;
   (viii) L18F, D80A, D215G, a LAL242-244 deletion, R246I, K417N, E484K, N501Y, D614G, and A701V;
   (ix) D80A, K417N, E484K, N501Y, D614G, and A701V;
   (x) L18F, T20N, P26S, D138Y, R190S, K417T, E484K, N501Y, D614G, H655Y, T1027I, and V1176F; and
   (xi) L18F, T20N, P26S, D138Y, R190S, K417T, E484K, N501Y, D614G, H655Y, T1027I.

9. The method of claim 1, wherein the plasmonic substrate further comprises at least one antigen selected from a MERS antigen, and wherein the plasmonic substrate further comprises a common cold antigen selected from the group consisting of human coronavirus 229E, human coronavirus NL63, human coronavirus OC43, and human coronavirus HKU1.

10. The method of claim 1, wherein the organic dyes are selected from the group consisting of Cy3, Cy5, CF647, IRdye800, IR820, iFluo820, and combinations thereof.

11. The method of claim 1, further comprising adding a protein denaturing agent to the saliva sample in step (a).

12. The method of claim 11, wherein the protein denaturing agent is selected from the group consisting of urea, formamide, guanidine, sodium salicylate, dimethyl sulfoxide, propylene glycol, and combinations thereof.

13. The method of claim 12, wherein the protein denaturing agent is urea or formamide.

14. The method of claim 1, further comprising after step (b) adding a protein denaturing agent to destabilize the immune complexes; and removing the protein denaturing agent, and thereby removing unbound and low avidity antibodies.

15. The method of claim 14, wherein the protein denaturing agent is selected from urea, formamide, guanidine, sodium salicylate, dimethyl sulfoxide, propylene glycol, and combinations thereof.

16. The method of claim 15, wherein the protein denaturing agent is urea or formamide.

17. The method of claim 1, wherein the saliva sample is collected in a local or remote lab, office, or home and mailed to a clinical lab for testing antibodies against SARS-CoV-2 and other coronaviruses.

18. The method of claim 1, wherein the organic dyes are selected from the group consisting of Cy3, Cy5, CF647, IR820, iFluo820, and combinations thereof.

19. The method of claim 1, wherein the organic dyes are selected from the group consisting of CF647 and IRdye800.

20. The method of claim 18, wherein the contacting the saliva sample to at least two SARS-CoV-2 antigens occurs for an incubation time of 60 minutes.

21. The method of claim 19, wherein the contacting the IgG, IgM, or IgA immune complexes with an organic dye labeled antihuman IgG, antihuman IgM and antihuman IgA antibodies occurs for an incubation time of about 30 minutes.

22. A method of diagnosing or prognosticating recent or remote SARS-CoV-2 infection in a subject in need thereof, wherein the subject was recently infected, remotely infected, or recently and remotely infected; the method comprising:
(a) obtaining, or having obtained, a saliva sample from the subject;
(b) diluting the saliva sample two times in a buffer solution;
(c) contacting the saliva sample to at least two SARS-CoV-2 antigens, wherein the at least two SARS-CoV-2 antigens are bound on a plasmonic substrate, and wherein the at least two SARS-CoV-2 antigens specifically bind to at least two IgM, IgG, IgA antibody in the saliva sample to form immune complexes, and wherein the plasmonic substrate is present in a multiple well format such that duplicate substrates are located side-by-side,
(d) adding a protein denaturing agent to one of the duplicate substrates either prior to or after step (c), to destabilize the immune complexes, removing the protein denaturing agent, thereby removing unbound and low avidity antibodies,
(e) contacting the IgG, IgM, or IgA immune complexes with an organic dye labeled antihuman IgG, antihuman IgM and antihuman IgA antibodies, wherein the organic dye labeled antihuman IgG, antihuman IgM, and antihuman IgA antibodies are each labeled with a different organic dye that fluoresces at a non-overlapping emission wavelength, and
(f) detecting fluorescence intensities of the organic dyes to diagnose SARS-CoV-2 infection, COVID-19, or a combination of SARS-CoV-2 infection and COVID-19, wherein the fluorescence intensity is proportional to the amount of IgM, IgG, or IgA antibody in the sample, and wherein the amount of IgM, IgG, or IgA antibody in the sample indicates the time since SARS-CoV-2 infection,
(g) evaluating the amount of bound antibody in the duplicate side-by-side substrates to determine avidity, wherein avidity is determined by evaluating the ratio of the IgG level measured in the presence of denaturing agent to the IgG level measured in the absence of denaturing agent, wherein
when the ratio is 0.4 to 0.6 or less, the avidity is low; and when the ratio is 0.4 to 0.6 or greater, the avidity is high; and wherein when the avidity is low, the infection is recent; and when the avidity is high, the infection is old; and
(h) treating the subject diagnosed with SARS-CoV-2 infection, COVID-19, or a combination of SARS-CoV-2 infection and COVID-19, with a compound or other therapy to mitigate symptoms, prevent spread of SARS-CoV-2 infection, facilitate therapy for others, improve symptoms of COVID-19, or a combination thereof.

23. The method of claim 22, wherein the plasmonic substrate is a plasmonic gold, silver, aluminum, copper, glass, quartz, plastic or nitrocellulose substrate.

24. The method of claim 23, wherein the substrate comprises a metallic film arranged discontinuously on the substrate, wherein the metallic film has isolated island areas of between about 100 nm$^2$ and 250,000 nm$^2$ in surface-exposed area, the isolated islands being separated by gaps of about 10 to about 60 nm.

25. The method of claim 24, wherein the plasmonic substrate is a plasmonic gold substrate.

26. The method of claim 22, wherein the at least two SARS-CoV-2 antigens are selected from the group consisting of S1, RBD, S2, nucleocapsid antigen, and combinations thereof.

27. The method of claim 26, wherein the at least two SARS-CoV-2 antigens are SARS-CoV-2 S1 and RBD.

28. The method of claim 22, wherein the at least two SARS-CoV-2 antigens are a SARS-CoV-2 antigen variant selected from the group consisting of variants:
(i) N501Y;
(ii) K417N, E484K, and N501Y;
(iii) E484K; K417N;
(iv) L452R and E484Q;
(v) K417T, E484K, and N501Y;
(vi) K417T;
(vii) HV69-70 deletion, a Y144 deletion, N501Y, A570D, D614G, P681H, T716I, S982A, and D1118H;
(viii) L18F, D80A, D215G, a LAL242-244 deletion, R246I, K417N, E484K, N501Y, D614G, and A701V;
(ix) D80A, K417N, E484K, N501Y, D614G, and A701V;
(x) L18F, T20N, P26S, D138Y, R190S, K417T, E484K, N501Y, D614G, H655Y, T1027I, and V1176F; and
(xi) L18F, T20N, P26S, D138Y, R190S, K417T, E484K, N501Y, D614G, H655Y, T1027I.

29. The method of claim 22, wherein the plasmonic substrate further comprises at least one antigen selected from a MERS antigen, and wherein the plasmonic substrate further comprises at least one common cold antigen selected from group consisting of human coronavirus 229E, human coronavirus NL63, human coronavirus OC43, and human coronavirus HKU1.

* * * * *